United States Patent [19]

Kathawala

[11] Patent Number: 4,822,799
[45] Date of Patent: Apr. 18, 1989

[54] PYRAZOLOPYRIDINE ANALOGS OF MEVALONOLACTONE AND DERIVATIVES THEREOF USEFUL FOR INHIBITING CHOLESTEROL BIOSYNTHESIS IN MAMMALS

[75] Inventor: Faizulla G. Kathawala, Mountain Lakes, N.J.

[73] Assignee: Sandoz Pharm. Corp., E. Honover, N.J.

[21] Appl. No.: 149,232

[22] Filed: Jan. 27, 1988

[51] Int. Cl.$^4$ ............... C07D 471/04; A61K 31/395
[52] U.S. Cl. ..................................... 514/303; 546/119
[58] Field of Search ......................... 546/119; 514/303

[56] References Cited

U.S. PATENT DOCUMENTS

| | | | |
|---|---|---|---|
| 4,248,889 | 2/1981 | Oka et al. | 424/308 |
| 4,255,444 | 3/1981 | Oka et al. | 424/279 |
| 4,293,496 | 10/1981 | Willard | 260/343.5 |
| 4,459,422 | 7/1984 | Willard et al. | 560/59 |
| 4,479,965 | 10/1984 | Terahara et al. | 424/279 |
| 4,571,428 | 2/1986 | Kapa | 556/437 |
| 4,588,715 | 5/1986 | Damon | 514/63 |
| 4,613,610 | 9/1986 | Wareing | 514/406 |
| 4,647,576 | 3/1987 | Hoefle et al. | 514/422 |
| 4,751,235 | 6/1988 | Anderson | 514/299 |
| 4,755,606 | 7/1988 | Wareing | 548/110 |

FOREIGN PATENT DOCUMENTS

84/02131  6/1984  World Int. Prop. O.
87/02662  5/1987  World Int. Prop. O.

OTHER PUBLICATIONS

Hulcher, Arch. Biochem. Biophys. 146, 422–427 (1971).
Sato et al., Chem. Pharm. Bull. (Tokyo) 28, 1509–1525 (1980).
Singer et al., Proc. Soc. Exp. Biol. Med. 102, 370–373 (1959).

Primary Examiner—Mary C. Lee
Assistant Examiner—John A. H. Russell
Attorney, Agent, or Firm—Gerald D. Sharkin; Richard E. Vila; Melvyn M. Kassenoff

[57] ABSTRACT

Compounds of the formula

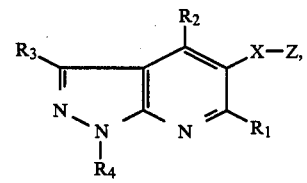

and processes for and intermediates in the synthesis thereof, pharmaceutical compositions comprising such a compound and the use of such compounds for inhibiting cholesterol biosynthesis and lowering the blood cholesterol level and, therefore, in the treatment of hyperlipoproteinemia and atherosclerosis.

20 Claims, No Drawings

PYRAZOLOPYRIDINE ANALOGS OF MEVALONOLACTONE AND DERIVATIVES THEREOF USEFUL FOR INHIBITING CHOLESTEROL BIOSYNTHESIS IN MAMMALS

This invention relates to compounds of the formula

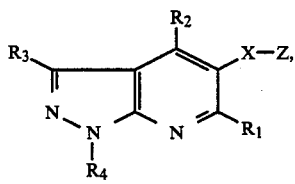 (I)

wherein $R_1$ is $C_{1-6}$alkyl not containing an asymmetric carbon atom, $C_{5-7}$cycloalkyl, ($C_{5-7}$cycloalkyl)methyl, phenyl-$(CH_2)_m$-, pyridyl-2, pyridyl-3, pyridyl-4, thienyl-2, thienyl-3 or

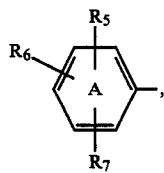

$R_2$ is $C_{1-6}$alkyl not containing an asymmetric carbon atom, $C_{5-7}$cycloalkyl, ($C_{5-7}$cycloalkyl)methyl, phenyl-$(CH_2)_m$-, pyridyl-2, pyridyl-3, pyridyl-4, thienyl-2, thienyl-3 or

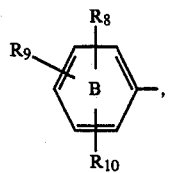

with the proviso that not more than one of $R_1$ and $R_2$ is a member of the group consisting of pyridyl-2, pyridyl-3, pyridyl-4, thienyl-2, thienyl-3, Ring A and Ring B, $R_3$ is $C_{1-6}$alkyl not containing an asymmetric carbon atom, $C_{5-7}$cycloalkyl or

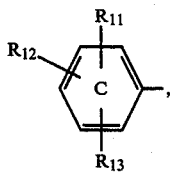

$R_4$ is $C_{1-6}$alkyl not containing an asymmetric carbon atom, $C_{5-7}$cycloalkyl or

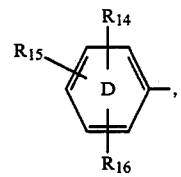

X is $-(CH_2)_n-$, $-CH=CH-$, $-CH_2-CH=CH-$ or $-CH=CH-CH_2-$, wherein n is 1, 2 or 3, and Z is

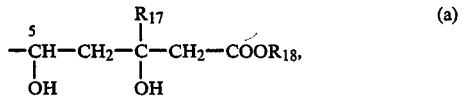 (a)

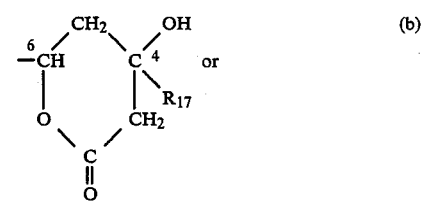 (b)

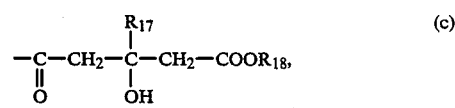 (c)

wherein
$R_{17}$ is hydrogen, or $C_{1-3}$alkyl, and
$R_{18}$ is hydrogen, $R_{19}$ or M,
wherein
$R_{19}$ is a physiologically acceptable ester group, and
M is a pharmaceutically acceptable cation,
with the proviso that Z may be a group of the formula

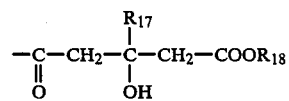

only when (i) X is $-CH=CH-$ or $-CH_2-CH=CH-$, (ii) $R_{17}$ is $C_{1-3}$alkyl or (iii) both (i) and (ii), wherein
each of $R_5$, $R_8$, $R_{11}$ and $R_{14}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy,
each of $R_6$, $R_9$, $R_{12}$ and $R_{15}$ is independently hydrogen, $C_{1-3}$alkyl, $C_{1-3}$alkoxy, trifluoromethyl, fluoro, chloro, phenoxy or benzyloxy, and
each of $R_7$, $R_{10}$, $R_{13}$ and $R_{16}$ is independently hydrogen, $C_{1-2}$alkyl, $C_{1-2}$alkoxy, fluoro or chloro, with the provisos that not more than one substituent on each of Rings A, B, C and D independently is trifluoromethyl, not more than one substituent on each of Rings A, B, C and D independently is phenoxy, and not more than one substituent on each of Rings A, B, C and D independently is benzyloxy, and
each m is independently 1, 2 or 3,
processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable ester group" is meant a group which, together with the —COO— radical to which it is attached, forms an ester group which is physiologically acceptable. The preferred such groups are the physiologically acceptable and hydrolyzable ester groups. By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R_{18}$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R'_{19}$.

For the avoidance of doubt, throughout this specification it is the right-hand side of the X radical that is attached to the Z group.

As is self-evident to those in the art, each compound of Formula I wherein Z is a group of Formula a or b has two centers of asymmetry (the two carbon atoms bearing the hydroxy groups in the group of Formula a and the carbon atom bearing the hydroxy group and the carbon atom having the free valence in the group of Formula b) and, therefore, there are four stereoisomeric forms (enantiomers) of each compound (two racemates or pairs of diastereoisomers), provided that $R_{18}$ does not contain any center of asymmetry. The four stereoisomers may be designated as the R,R, R,S, S,R and S,S enantiomers, all four stereoisomers being within the scope of this invention. When $R_{18}$ contains one or more centers of asymmetry, there are eight or more stereoisomers, all being within the scope of this invention. On the other hand, each compound of Formula I wherein Z is a group of Formula c has a single center of asymmetry (the carbon atom bearing the hydroxy group in the group of Formula c) and, therefore, there are two enantiomers of each compound, provided that $R_{18}$ does not contain any center of asymmetry. The two stereoisomers may be designated as the 3R and 3S enantiomers, both being within the scope of this invention. When $R_{18}$ contains one or more centers of asymmetry, there are four or more stereoisomers, all being within the scope of this invention. Since it is preferred that $R_{18}$ not contain a center of asymmetry and for reasons of simplicity, in both cases any additional stereoisomers resulting from the presence of one or more centers of asymmetry in $R_{18}$ will be ignored, it being assumed that $R_{18}$ is free of centers of asymmetry.

The compounds of Formula I may be divided into three groups, viz., those of Groups IA, IB and IC:

| | $R_1$ | $R_2$ |
|---|---|---|
| IA | Other than Ring A, pyridyl and thienyl | Ring B, pyridyl or thienyl |
| IB | Ring A, pyridyl or thienyl | Other than Ring B, pyridyl and thienyl |
| IC | Other than Ring A, pyridyl and thienyl | Other than Ring B, pyridyl and thienyl |

The compounds of each of Groups IA, IB and IC may be divided into three subgroups based upon the significance of Z, viz., Group IAa (the compounds of Group IA wherein Z is a group of Formula a), Group IAb (the compounds of Group IA wherein Z is a group of Formula b), Group IAc (the compounds of Group IA wherein Z is a group of Formula c), Group IBa (the compounds of Group IB wherein Z is a group of Formula a), Group IBb (the compounds of Group IB wherein Z is a group of Formula b), Group IBc (the compounds of Group IB wherein Z is a group of Formula c), Group ICa (the compounds of Group IC wherein Z is a group of Formula a), Group ICb (the compounds of Group IC wherein Z is a group of Formula b) and Group ICc (the compounds of Group IC wherein Z is a group of Formula c).

Preferably, one of $R_1$ and $R_2$ is $C_{1-6}$alkyl not containing an asymmetric carbon atom and the other is Ring A (if $R_1$) or Ring B (if $R_2$). Also preferably, at least one of $R_3$ and $R_4$ is $C_{1-6}$alkyl not containing an asymmetric carbon atom, more preferably $C_{1-3}$alkyl and most preferably $C_{1-2}$alkyl. More preferably, the preferences of both preceding sentences occur simultaneously. Thus, the preferred compounds of Formula I and the subscopes thereof are those having attached to the pyrazolopyridine ring (i) Ring A or Ring B and (ii) three alkyl groups or Ring C or Ring D and two alkyl groups. The more preferred compounds of Formula I and the subscopes thereof are those having attached to the pyrazolopyridine ring Ring B and three alkyl groups or Rings B and C and two alkyl groups.

In Group IA:

$R_1$ is preferably $R_{1A}$, where $R_{1A}$ is $C_{1-6}$alkyl not containing an asymmetric carbon atom, more preferably $R'_{1A}$, where $R'_{1A}$ is $C_{1-4}$alkyl not containing an asymmetric carbon atom, even more preferably where $R''_{1A}$, where $R''_{1A}$ is $C_{1-3}$alkyl, and most preferably i-propyl; and $R_2$ is preferably $R_{2A}$, where $R_{2A}$ is Ring B, more preferably $R'_{2A}$, where $R'_{2A}$ is Ring B wherein $R_8$ is $R'_8$, $R_9$ is $R'_9$, and $R_{10}$ is $R'_{10}$, even more preferably $R''_{2A}$, where $R''_{2A}$ is Ring B wherein $R_8$ is $R''_8$, $R_9$ is $R''_9$, and $R_{10}$ is hydrogen, and most preferably phenyl, 4-fluorophenyl or 3,5-dimethylphenyl, especially 4-fluorophenyl.

In Group IB:

$R_1$ is preferably $R_{1B}$, where $R_{1B}$ is Ring A, more preferably $R'_{1B}$, where $R'_{1B}$ is Ring A wherein $R_5$ is $R'_5$, $R_6$ is $R'_6$, and $R_7$ is $R'_7$, even more preferably $R''_{1B}$, where $R''_{1B}$ is Ring A wherein $R_5$ is $R''_5$, $R_6$ is $R''_6$, and $R_7$ is hydrogen, and most preferably phenyl, 4-fluorophenyl or 3,5-dimethylphenyl, especially 4-fluorophenyl; and $R_2$ is preferably $R_{2B}$, where $R_{2B}$ is $C_{1-6}$alkyl not containing an asymmetric carbon atom, more preferably $R'_{2B}$, where $R'_{2B}$ is $C_{1-4}$alkyl not containing an asymmetric carbon atom, even more preferably $R''_{2B}$, where $R''_{2B}$ is $C_{1-3}$alkyl, and most preferably i-propyl.

In Group IC:

$R_1$ is preferably $R_{1C}$, where $R_{1C}$ is $C_{1-6}$alkyl not containing an asymmetric carbon atom, more preferably $R'_{1C}$, where $R'_{1C}$ is $C_{1-4}$alkyl not containing an asymmetric carbon atom, even more preferably $R''_{1C}$, where $R''_{1C}$ is $C_{1-3}$alkyl, and most preferably i-propyl; and $R_2$ is preferably $R_{2C}$, where $R_{2C}$ is $C_{1-6}$alkyl not containing an asymmetric carbon atom, more preferably $R'_{2C}$, where $R'_{2C}$ is $C_{1-4}$alkyl not containing an asymmetric carbon atom, even more preferably $R''_{2C}$, where $R''_{2C}$ is $C_{1-3}$alkyl, and most preferably i-propyl.

In each group:

$R_3$ is preferably $R'_3$, where $R'_3$ is $C_{1-4}$alkyl not containing an asymmetric carbon atom or Ring C wherein $R_{11}$ is $R'_{11}$, $R_{12}$ is $R'_{12}$, and $R_{13}$ is $R'_{13}$, more preferably $R''_3$, where $R''_3$ is $C_{1-3}$alkyl or Ring C wherein $R_{11}$ is $R''_{11}$, $R_{12}$ is $R''_{12}$, and $R_{13}$ is hydrogen, even more preferably $R'''_3$, and where $R'''_3$ is $C_{1-2}$alkyl, and most preferably methyl.

$R_4$ is preferably $R'_4$, where $R'_4$, is $C_{1-4}$alkyl not containing an asymmetric carbon atom, more preferably $R''_4$, where $R''_4$ is $C_{1-3}$alkyl, even more preferably $R'''_4$, where $R'''_4$ is $C_{1-2}$alkyl, and most preferably methyl.

Each of $R_5$, $R_8$, $R_{11}$ and $R_{14}$ is preferably $R'_5$, $R'_8$, $R'_{11}$ and $R'_{14}$, respectively, where each of $R'_5$, $R'_8$, $R'_{11}$ and $R'_{14}$ is independently hydrogen, $C_{1-3}$alkyl, $C_{1-2}$alkoxy, trifluoromethyl, fluoro or chloro, and more preferably $R''_5$, $R''_8$, $R''_{11}$ and $R_{14}$, respectively, where each of $R''_5$, $R''_8$, $R''_{11}$ and $R''_{14}$ is independently hydrogen, methyl or fluoro. $R''_5$ and $R''_8$ are most preferably fluoro, especially 4-fluoro, and $R''_{11}$ and $R''_{14}$ are most preferably hydrogen.

Each of $R_6$, $R_9$, $R_{12}$ and $R_{15}$ is preferably $R'_6$, $R'_9$, $R'_{12}$ and $R'_{15}$, respectively, where each of $R'_6$, $R'_9$, $R'_{12}$ and $R'_{15}$ is independently hydrogen, $C_{1-2}$alkyl, fluoro or chloro, more preferably $R''_6$, $R''_9$, $R''_{12}$ and $R''_{15}$, respectively, where each of $R''_6$, $R''_9$, and $R''_{15}$ is independently hydrogen or methyl, and most preferably hydrogen.

Each of $R_7$, $R_{10}$, $R_3$ and $R_{16}$ is preferably $R'_7$, $R'_{10}$, $R'_{13}$ and $R'_{16}$, respectively, where each of $R'_7$, $R'_{10}$, $R'_{13}$ and $R'_{16}$ is independently hydrogen or methyl, and most preferably hydrogen.

Preferably, each of Rings A, B, C and D independently bears a maximum of one substituent selected from the group consisting of t-butyl, trifluoromethyl, phenyl, phenoxy and benzyloxy. More preferably, when any two or all three of the substituents on Ring A [$R_5$, ($R'_5$, etc.), $R_6$ ($R'_6$, etc.) and $R_7$ ($R'_7$, etc.)], Ring B [$R_8$, ($R'_8$, etc.), $R'_9$ ($R'_9$, etc.) and $R_{10}$ ($R'_{10}$, etc.)], Ring C [$R_{11}$, ($R'_{11}$, etc.), $R_{12}$ ($R'_{12}$, etc.) and $R_{13}$ ($R'_{13}$, etc.)] and Ring D [$R_{14}$, ($R'_{14}$, etc.), $R_{15}$ ($R'_{15}$, etc.) and $R_{16}$ ($R'_{16}$, etc.)] independently are ortho to each other, at least one member of each pair that are ortho to each other is a member of the group consisting of hydrogen, methyl, methoxy, fluoro and chloro. Also more preferably, at least one of the ortho positions of each of Rings A, B, C and D independently has a member of the group consisting of hydrogen, fluoro and methyl.

Each of Rings A and B independently is preferably phenyl, 4-fluorophenyl or 3,5-dimethylphenyl and most preferably 4-fluorophenyl.

Each of Rings C and D is preferably phenyl.

$R_{17}$ is preferably $R'_{17}$, where $R'_{17}$ is hydrogen or methyl, and most preferably hydrogen.

$R_{18}$ is preferably $R'_{18}$, where $R'_{18}$ is hydrogen, $R'_{19}$ or M, more preferably $R''_{18}$, where $R''_{18}$ is hydrogen, $C_{1-3}$alkyl or M, even more preferably $R'''_{18}$, where $R'''_{18}$ is hydrogen, $C_{1-2}$alkyl or M, and most preferably M, particularly M' and especially sodium.

$R_{19}$ is preferably a physiologically acceptable and hydrolyzable ester group, more preferably $R'_{19}$, where $R'_{19}$ is $C_{1-3}$alkyl, n-butyl, i-butyl, t-butyl or benzyl, even more preferably $R''_{19}$, where $R''_{19}$ is $C_{1-3}$alkyl, and most preferably $R'''_{19}$, where $R'''$ is $C_{1-2}$alkyl, especially ethyl.

Any —CH=CH—, —CH=CH—CH$_2$— or —CH$_2$—CH=CH— as X is preferably trans, i.e., (E).

X is preferably X', where X' is —CH$_2$CH$_2$13 or —CH=CH—, and most preferably

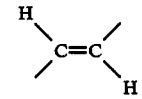

(i.e., (E)—CH+CH—).

Z is preferably a group of Formula a or c wherein $R_{17}$ is $R'_{17}$ (especially hydrogen), and $R_{18}$ is $R'_{18}$ or a group of Formula b wherein $R_{17}$ is $R'_{17}$ (especially hydrogen), more preferably a group of Formula a wherein $R_{17}$ is hydrogen, and $R_{18}$ is $R''_{18}$ or a group of Formula b wherein $R_{17}$ is hydrogen, even more preferably a group of Formula a wherein $R_{17}$ is hydrogen, and $R_{18}$ is $R'''_{18}$ or a group of Formula b wherein $R_{17}$ is hydrogen, and most preferably a group of Formula a wherein $R_{17}$ is hydrogen, and $R_{18}$ is M, preferably M' and especially sodium.

m is preferably m', where m' is 1 or 2, and most preferably 1.

n is preferably n', where n' is 2 or 3, and most preferably 2.

M is preferably free from centers of asymmetry and is more preferably M', i.e., sodium, potassium or ammonium, and most preferably sodium. For simplicity, each formula in which M appears has been written as if M were monovalent and, preferably, it is. However, it may also be divalent or trivalent and, when it is, it balances the charge of two or three carboxy groups, respectively. Thus, Formula I and every other formula containing an M embrace compounds wherein M is divalent or trivalent, i.e., compounds containing two or three carboxylate-containing anions per cation M.

As between otherwise identical compounds of Formula I, those wherein Z is a group of Formula a are generally preferred over those wherein it is a group of Formula b or c, with those wherein Z is a group of Formula b being preferred over those wherein it is a group of Formula c.

Insofar as the compounds of Groups IAa, IBa and ICa and each of the subgroups thereof are concerned, the erythro isomers are preferred over the threo isomers, erythro and threo referring to the relative positions of the hydroxy groups in the 3- and 5-positions of the group of Formula a.

Insofar as the compounds of Groups IAb, IBb and ICb and each of the subgroups thereof are concerned, the trans lactones are generally preferred over the cis lactones, cis and trans referring to the relative positions of $R_{17}$ and the hydrogen atom in the 6-position of the group of Formula b.

The preferred stereoisomers of the compounds of Formula I having only two centers of asymmetry wherein X is —CH=CH— or —CH$_2$—CH=CH—, and Z is a group of Formula a are the 3R,5S isomers and the racemate of which each is a constituent, i.e., the 3R,5S-3S,5R (erythro) racemates, especially the 3R,5S isomers.

The preferred stereoisomers of the compounds of Formula I having only two centers of asymmetry wherein X is —(CH$_2$)$_n$— or —CH=CH—CH$_2$—, and Z is a group of Formula a are the 3R,5R isomers and the racemate of which each is a constituent, i.e., the 3R,5R-3S,5S (erythro) racemates, especially the 3R,5R isomers.

The preferences set forth in the preceding two paragraphs also apply to the compounds of Groups IAa, IBa and ICa having more than two centers of asymmetry and represent the preferred configurations of the indicated positions.

The preferred stereoisomers of the compounds of Formula I wherein X is —CH=CH— or —CH$_2$—CH=CH—, and Z is a group of Formula b are the 4R,6S isomers and the racemate of which each is a constituent, i.e., the 4R,6S-4S,6R (trans lactone) racemates, especially the 4R,6S isomers.

The preferred stereoisomers of the compounds of Formula I wherein X is —(CH$_2$)$_n$— or —CH=CH—CH$_2$—, and Z is a group of Formula b are the 4R,6R isomers and the racemate of which each is a constituent, i.e., the 4R,6R-4S,6S (trans lactone) racemates, especially the 4R,6R isomers.

The preferred stereoisomers of the compounds of Formula I having only one center of asymmetry wherein Z is a group of Formula c are the 3R isomers. This preference also applies to the compounds of Groups IAc, IBc and ICc having more than one center of asymmetry and represents the preferred configuration of the indicated position.

Each of the preferences set forth above applies, not only to the compounds of Formula I, but also to the compounds of Groups IA, IB and IC and those of Groups IAa, IAb, IAc, IBa, IBb, IBc, ICa, ICb and ICc as well as to every other subgroup thereof set forth in the specification, e.g., Groups (i) et seq., unless otherwise indicated. When any preference or group contains a variable, the preferred significances of that variable apply to the preference or group in question, unless otherwise indicated. Preferred groups of compounds of Groups IAa, IAb, IAc, IBa, IBb, IBc, ICa, ICb and ICc include the compounds (i) of Group IAa wherein $R_1$ is $R_{1A}$, $R_2$ is $R_{2A}$, $R_3$ is $R'_3$, $R_4$ is $R'_4$, $R_{17}$ is $R'_{17}$, $R_{18}$ is $R'_{18}$, and X is X', (ii) of (i) wherein $R_1$ is $R'_{1A}$, $R_2$ is $R'_{2A}$, $R_3$ is R"$_3$, $R_4$ is R"$_4$, $R_{17}$ is hydrogen, $R_{18}$ is R"$_{18}$, and X is (E)—CH=CH—, (iii) of (ii) wherein $R_1$ is R"$_{1A}$, and $R_{18}$ is R'''$_{18}$, especially M, (iv) of (iii) wherein $R_2$ is R"$_{2A}$, $R_3$ is R'''$_3$, and $R_4$ is R'''$_4$, (v) of (iv) wherein $R_{18}$ is M, particularly M' and especially sodium, (vi) of Group IAb wherein $R_1$ is $R_{1A}$, $R_2$ is $R_{2A}$, $R_3$ is $R'_3$, $R_4$ is $R'_4$, $R_{17}$ is $R'_{17}$, and X is X', (vii) of (vi) wherein $R_1$ is $R'_{1A}$, $R_2$ is $R'_{2A}$, $R_3$ is R"$_3$, $R_4$ is R"$_4$, $R_{17}$ is hydrogen, and X is (E)—CH=CH—, (viii) of (vii) wherein $R_1$ is R"$_{1A}$, (ix) of (viii) wherein $R_2$ is R"$_{2A}$, $R_3$ is R'''$_3$, and $R_4$ is R'''$_4$, (x)-(xiv) of Group IAc which correspond to Groups (i)-(v), i.e., wherein the variables are as defined in said groups, (xv) of Group IBa wherein $R_1$ is $R_{1B}$, $R_2$ is $R_{2B}$, $R_3$ is $R'_3$, $R_4$ is $R'_4$, $R_{17}$ is $R'_{17}$, $R_{18}$ is $R'_{18}$, and X is X', (xvi) of (xv) wherein $R_1$ is $R'_{1B}$, $R_2$ is $R'_{2B}$, $R_3$ is R"$_3$, $R_4$ is R"$_4$, $R_{17}$ is hydrogen, $R_{18}$ is R"$_{18}$, and X is (E)—CH=CH—, (xvii) of (xvi) wherein $R_2$ is R"$_{2B}$, and $R_{18}$ is R'''$_{18}$, especially M, (xviii) of (xvii) wherein $R_1$ is R"$_{1B}$, $R_3$ is R'''$_3$, and $R_4$ is R'''$_4$, (xix) of (xviii) wherein $R_{18}$ is M, particularly M' and especially sodium, (xx) of Group IBb wherein $R_1$ is $R_{1B}$, $R_2$ is $R_{2B}$, $R_3$ is $R'_3$, $R_4$ is $R'_4$, $R_{17}$ is $R'_{17}$, and X is X', (xxi) of (xx) wherein $R_1$ is $R'_{1B}$, $R_2$ is $R'_{2B}$, $R_3$ is R"$_3$, $R_4$ is R"$_4$, $R_{17}$ is hydrogen, and X is (E)—CH=CH—, (xxii) of (xxi) wherein $R_2$ is R"$_{2B}$, (xxiii) of (xxii) wherein $R_1$ is R"$_{1B}$, $R_3$ is R'''$_3$, and $R_4$ is R'''$_4$, (xxiv)-(xxviii) of Group IBc which correspond to Groups (xv)-(xix), i.e., wherein the variables are as defined in said groups, (xxix) of Group ICa wherein $R_1$ is $R_{1C}$, $R_2$ is $R_{2C}$, $R_3$ is $R'_3$, $R_4$ is $R'_4$, $R_{17}$ is $R'_{17}$, $R_{18}$ is $R'_{18}$, and X is X', (xxx) of (xxix) wherein $R_1$ is $R'_{1C}$, $R_2$ is $R'_{2C}$, $R_3$ is R"$_3$, $R_4$ is R"$_4$, $R_{17}$ is hydrogen, $R_{18}$ is R"$_{18}$, and X is (E)—CH=CH—, (xxxi) of (xxx) wherein $R_1$ is R"$_{1C}$, $R_2$ is R"$_{2C}$, and $R_{18}$ is R'''$_{18}$, especially M, (xxxii) of (xxxi) wherein $R_3$ is R'''$_3$, and $R_4$ is R'''$_4$, (xxxiii) of (xxxii) wherein $R_{18}$ is M, particularly M' and especially sodium, (xxxiv) of Group ICb wherein $R_1$ is $R_{1C}$, $R_2$ is $R_{2C}$, $R_3$ is $R'_3$, $R_4$ is $R'_4$, $R_{17}$ is $R'_{17}$, and X is X', (xxxv) of (xxxiv) wherein $R_1$ is $R'_{1C}$, $R_2$ is $R'_{2C}$, $R_3$ is R"$_3$, $R_4$ is R"$_4$, $R_{17}$ is hydrogen, and X is (E)—CH=CH—, (xxxvi) of (xxxv) wherein $R_1$ is R"$_{1C}$, and $R_2$ is R"$_{2C}$, (xxxvii) of (xxxvi) wherein $R_3$ is R'''$_3$, and $R_4$ is R'''$_4$, (xxxviii)–(xlii) of Group ICc which correspond to Groups (xxix)14 (xxxiii), i.e., wherein the variables are as defined in said groups, (xliii)–(lvii) of (i)–(v), (xv)–(xix) and (xxix)–(xxxiii) wherein the hydroxy groups in the 3- and 5-positions of the group of Formula a have the erythro configuration, and (lviii)–(lxix) of (vi)–(ix), (xx)–(xxiii) and (xxxiv)–(xxxvii) wherein $R_{17}$ and the hydrogen atom in the 6-position of the group of Formula b are trans to each other, i.e., the trans lactones.

Groups (i)–(xlii) embrace each of the possible stereoisomers, racemates and mixtures of diastereoisomers.

mates of the compounds wherein X is —CH=CH—, and Groups (lviii), (lxii) and (lxvi) also embrace the 4R,6R and 4S,6S isomers and the 4R,6R-4S,6S racemates of the compounds wherein X is —CH$_2$CH$_2$—.

The compounds of Formula I may be synthesized as follows:

Reaction Scheme I

The compounds of Formula I wherein X is —(CH$_2$)$_n$— or (E)—CH=CH—, and Z is a group of Formula a wherein $R_{17}$ is hydrogen, and $R_{18}$ is $R'_{19}$ or $R_{17}$ is $R_{17a}$ and $R_{18}$ is $M_2^\oplus$ may be synthesized by the following series of reactions:

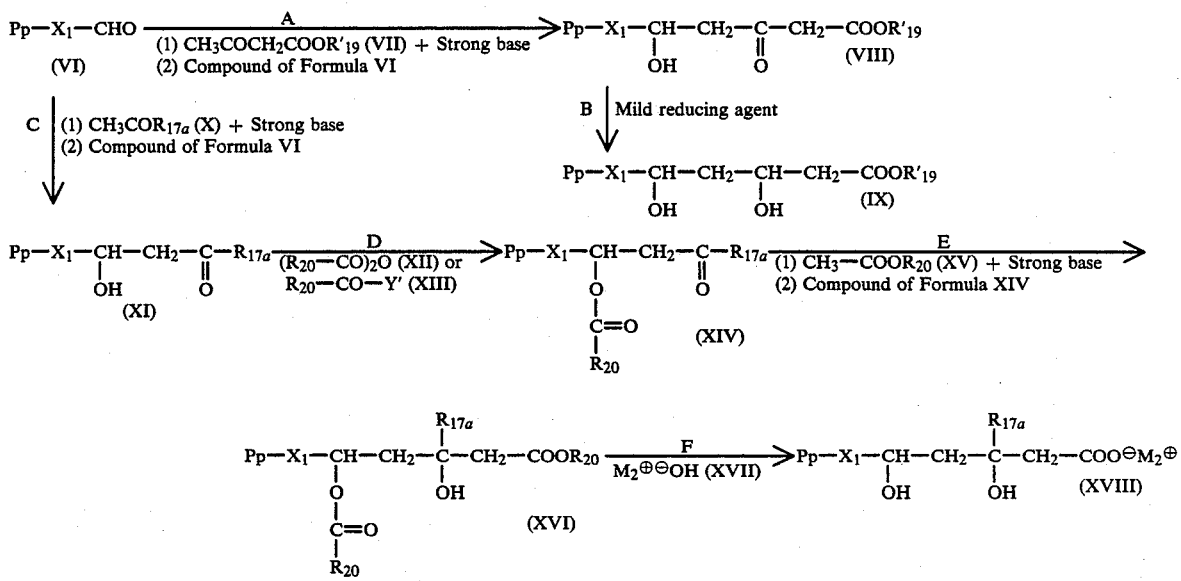

Groups (xliii)–(lvii) embrace the 3R,5S and 3S,5R isomers and the 3R,5S-3S,5R racemates of the compounds wherein X is —CH=CH—, and Groups (xliii), (xlviii) and (liii) also embrace the 3R,5R and 3S,5S isomers and the 3R,5R-3S,5S racemates of the compounds wherein X is —CH$_2$CH$_2$—. Groups (lviii)–(lxix) embrace the 4R,6S and 4S,6R isomers and the 4R,6S-4S,6R race-

Reaction Scheme II

The compounds of Formula I wherein X is —CH$_2$CH$_2$—, —CH$_2$CH$_2$CH$_2$—, —CH=CH—, —CH=CH—CH$_2$— or —CH$_2$—CH=CH—, and Z is a group of Formula a wherein $R_{18}$ is $R_{19'}$ may be synthesized by the following series of reactions:

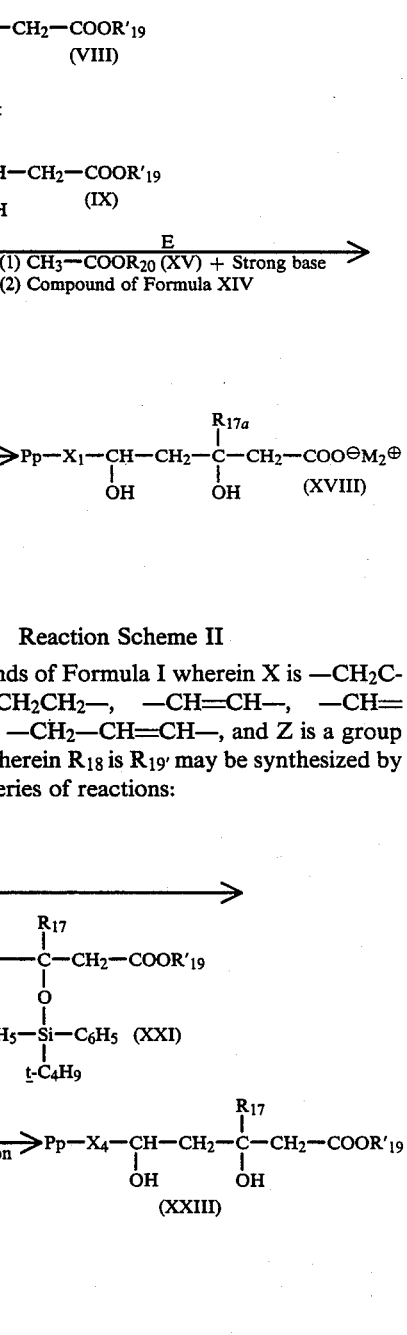

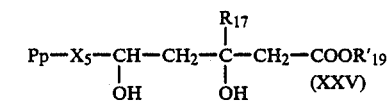

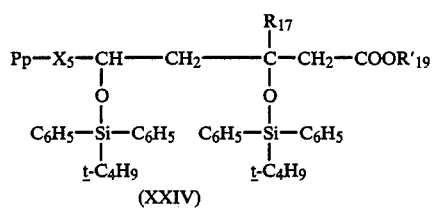

(XXV)

(XXIV)

Reaction Scheme III has a different significance of Formula a or b by following series of reactions:

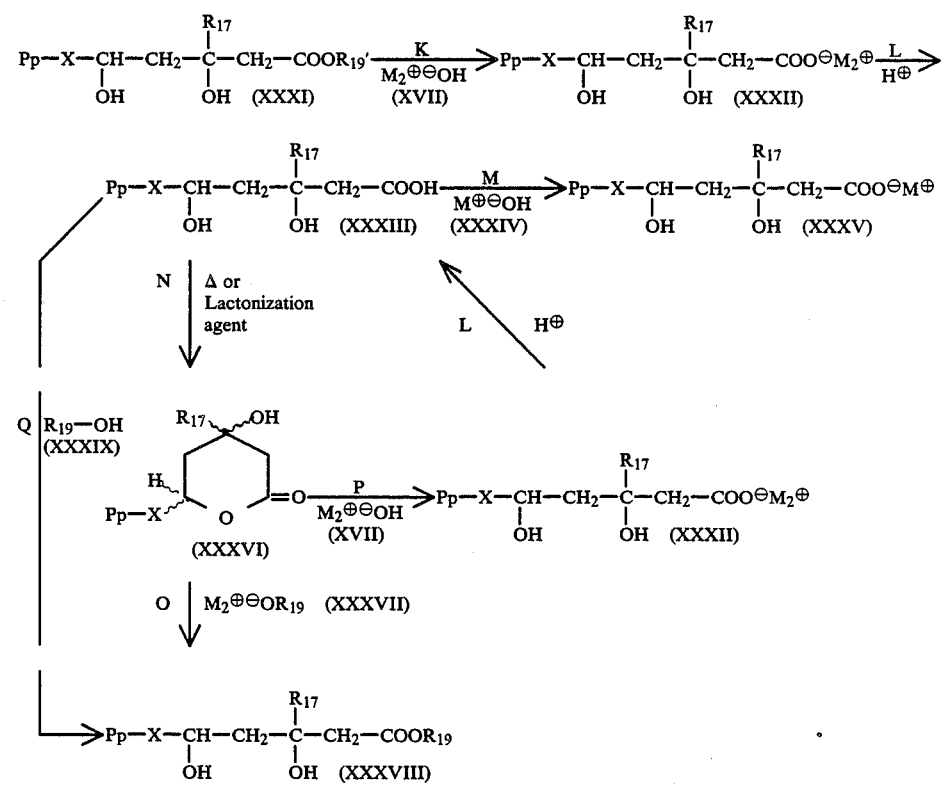

The compounds of Formula I wherein Z is a group of Formula a wherein $R_{18}$ is $R_{19}'$ may be converted into the corresponding compounds of Formula I wherein Z Reaction Scheme IV The compounds of Formula I wherein Z is a group of Formula c may be synthesized by the following series of reactions:

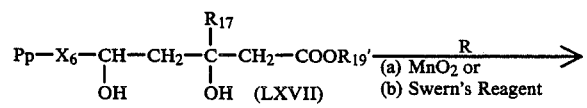

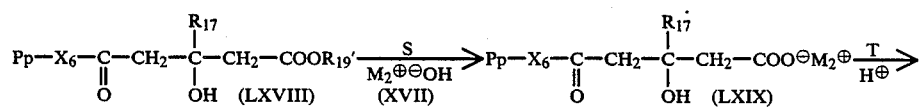

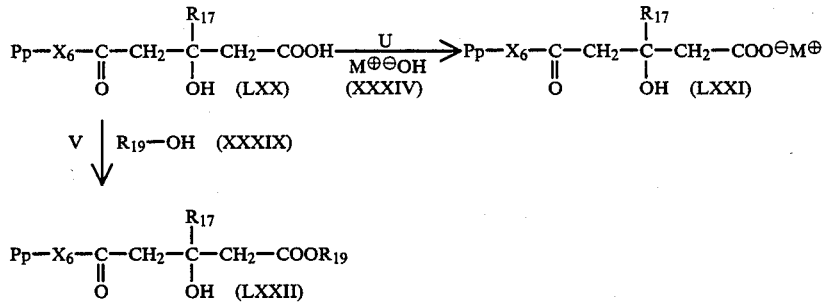
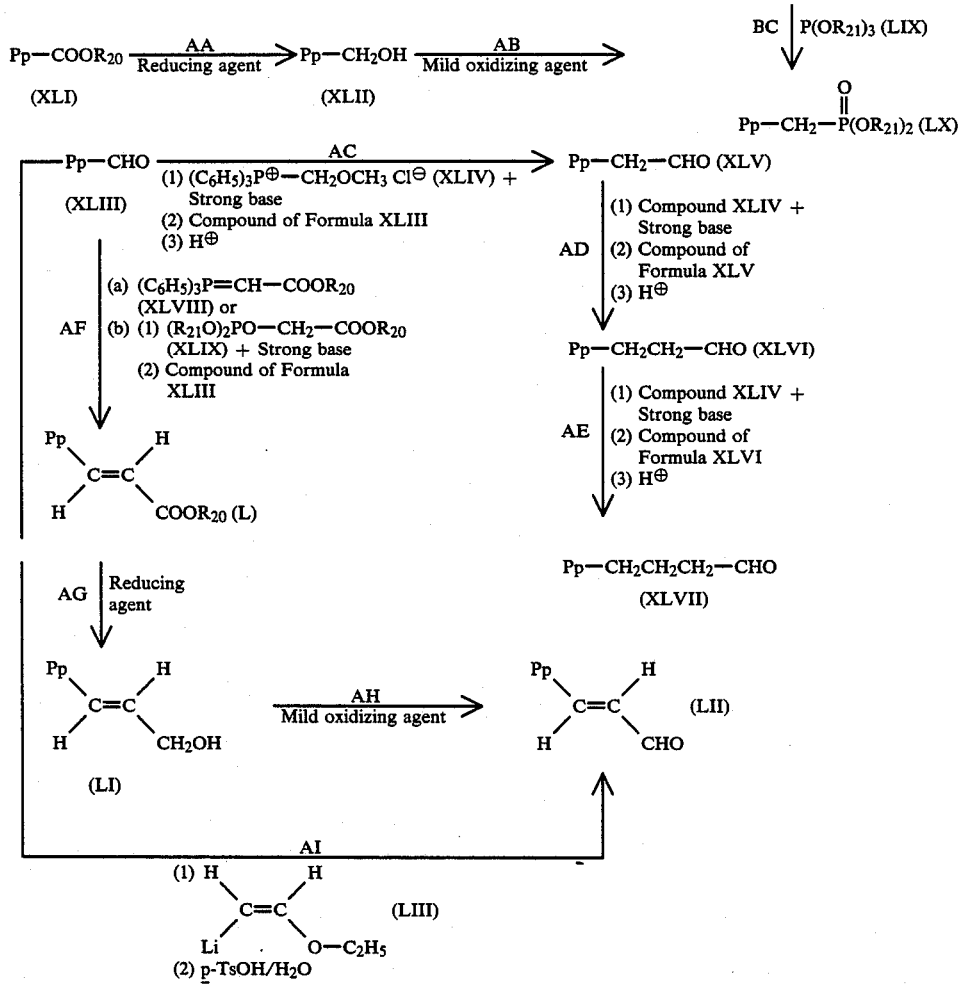
Reaction Scheme V
The compounds of Formula VI may be synthesized by the following series of reactions:
Reaction Scheme VI
The compounds of Formulae XIX, XX and XLI may be synthesized by the following series of reactions:
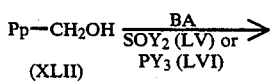
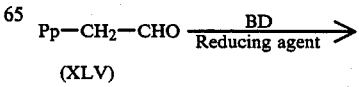

15

-continued

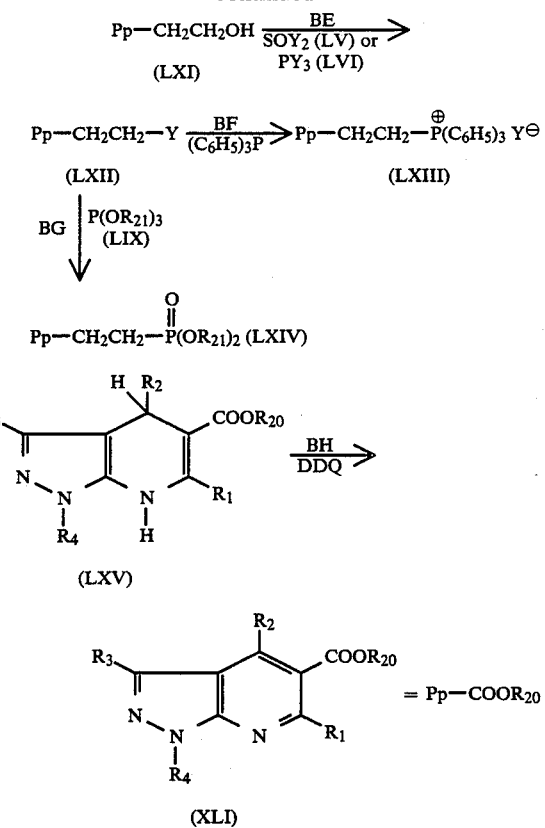

In the preceding reaction schemes,
Pp is

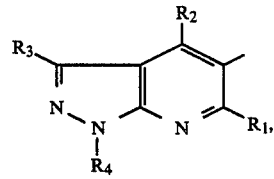

wherein $R_1$-$R_4$ are as defined above,
$R_{17a}$ is $C_{1-3}$alkyl,
each $R_{20}$ is independently $C_{1-3}$alkyl, preferably n-$C_{1-3}$alkyl, and most preferably $C_{1-2}$alkyl,
each $R_{21}$ is independently $C_{1-2}$alkyl, the two $C_{1-2}$alkyl groups preferably being the same,
$X_1$ is —$(CH_2)_n$— or (E)—CH=CH—, especially (E)—CH=CH—, wherein n is 1, 2 or 3,
$X_2$ is —$CH_2$— or —$CH_2CH_2$—,
$X_3$ is a direct bond or —$CH_2$—,
$X_4$ is —CH=CH—, —CH=CH—$CH_2$— or —$CH_2$—CH=CH—, preferably (E)—CH=CH—, (E)—CH=CH—$CH_2$— or (E)—$CH_2$—CH=CH— and especially (E)—CH=CH—,
$X_5$ is —$CH_2CH_2$— or —$CH_2CH_2CH_2$—, especially —$CH_2CH_2$—,
$X_6$ is —$(CH_2)_n$—, —CH=CH—, —$CH_2$—CH=CH— or —CH=CH—$CH_2$— when $R_{17}$ is $C_{1-3}$alkyl and is —CH=CH— or —$CH_2$—CH=CH— when $R_{17}$ is hydrogen, wherein n is 1, 2 or 3,
Y is chloro or bromo,
$Y^\ominus$ is chloride or bromide,
$M_2^\oplus$ is sodium or potassium, and
each of the other variables is as defined above.

| Reaction/Type | Reagents, Molar Ratios and Comments | Temperature | Time | Solvent | Inert Atmosphere |
|---|---|---|---|---|---|
| A | (1) Generation of dianion of VII: 2-2.4 equivalents strong base, pref. 1-1.1 moles sodium hydride then 1-1.1 moles n-butyllithium or 2-2.2 moles lithium diisopropylamide per mole VII. | −50°-10° C., pref. −20°-5° C. | 0.5-3 hrs. | AIO, e.g., ES, pref. THF | Yes (pref. argon) |
|  | (2) 1-4.5 moles, pref. 1.2-3.2 moles, more pref. 1.3-2.1 moles, dianion of VII (assuming 100% conversion of VII to its dianion) per mole VI. | −80°-0° C., pref. −50°-0° C., more pref. −30°-10° C. | 0.2-4 hrs., pref. 0.3-2.5 hrs. | Same as Step 1 | Yes (pref. argon) |
|  | (3) Quench with, e.g., saturated ammonium chloride solution. Product (VIII) is racemic. | Same as Step 2 | 1-5 min. | Same as Step 1 | — |
| B (Reduction) | (a) Non-stereoselective: 1-4, pref. 2-4, equivalents transferable hydride per mole VIII, pref. sodium borohydride or complex of t-butylamine and borane. When a racemic VIII is utilized, product (IX) is a mixture of all four possible stereoisomers (the erythro and threo racemates) wherein the ratio of the erythro stereoisomers to the threo stereoisomers is about 3:2-2:3. | −10°-30° C. | 1-8 hrs. | IO, e.g., lower alkanol, esp. ethanol | Yes |
|  | (b) Stereoselective: (1) 1-2.2 moles, pref. 1.02-2 moles, tri-(primary or secondary $C_{2-4}$alkyl)-borane, pref. triethylborane or tri-n-butylborane, and, optionally, air, e.g., 0.5-8 l., pref. 0.75-6.5 l., (at 25° C. and 760 mm. Hg.) per mole VIII. | 0°-50° C., pref. 0°-25° C. | 0.5-6 hrs., pref. 1-3.5 hrs. | AIO, pref. ES, esp. THF, or mixture of THF and methanol, pref. a 3-4:1 mixture | Pref. Yes |
|  | (2) 0.4-10 moles, pref. 1-10 moles, sodium borohydride per mole VIII. It may be necessary to complete the reaction at −50°-−10° C. After the reaction, quench reaction mixture with, for | −100°-−10° C., pref. −90°-−70° C. | 1-96 hrs., pref. 2-72 hrs. | Same as Step 1 | Pref. Yes |

-continued

| Reaction/Type | Reagents, Molar Ratios and Comments | Temperature | Time | Solvent | Inert Atmosphere |
|---|---|---|---|---|---|
| | example, 10% hydrochloric acid or saturated ammonium chloride solution and isolate crude product by extracting with a suitable inert organic solvent (e.g., diethyl ether) and evaporating the solvent at reduced pressure. It is pref. to crystallize the cyclic boron ester, if possible. | | | | |
| | (3) Large excess of anhydrous methanol, e.g., 50-100 moles per mole VIII. It is convenient to azeotrope a solution of the product of Step 2 in methanol three to four times. | 20°-60° C. | 0.5-16 hrs., pref. 1-4 hrs. | Neat | — |
| | When a racemic VIII is utilized in Alternative b, product (IX) is a mixture of the four possible stereoisomers wherein the ratio of the erythro isomers (racemate) to the threo isomers (racemate) is about 2-20:1, usually 5-15:1, when the solvent is THF. Repeated recrystallization of the cyclic boron ester produced in Step 2 of Alternative b, if a solid, may raise the ratio or even yield pure erythro racemate and mother liquors enriched with threo racemate. When, however, the solvent is a mixture of THF and methanol, said ratio may be as high as 50-100:1. | | | | |
| C | (1) Generation of monoanion of X: 1-1.1 equivalents strong base, pref. lithium diisopropylamide, per mole X. | −80°−−40° C., pref. −80°− −75° C. | 0.25-1.5 hrs. | AIO, e.g., ES, pref. THF | Yes |
| | (2) 1-4 moles, pref. 3 moles, monoanion of X (assuming 100% conversion of X to its monoanion) per mole VI. | −80°−−40° C., pref. −80°− −75° C. | 0.25-1.5 hrs. | Same as Step 1 | Yes |
| | (3) Quench with, for example, saturated ammonium chloride solution. Product (XI) is a racemate. | −80°-25° C. | 1-5 min. | — | — |
| D (Acylation) | 1-3 moles, pref. 2 moles, XII or XIII per mole XI. When an ES is used as the solvent, also use 1-4 moles, pref. 2.5-3 moles, of a tertiary amine, e.g., pyridine or, pref., 4-dimethylaminopyridine, per mole XI. Always use at least one mole of tertiary amine (when used) per mole XII or XIII | −10°-50° C., pref. 20°- 30° C. | 2-18 hrs., pref. 4-12 hrs. | Pyridine or anhydrous ES, pref. THF | Yes |
| E | (1) Generation of monoanion of XV: 1-1.1 equivalents strong base, pref. lithium diisopropylamide, per mole XV. | −80°-0° C. | 0.25-1 hr. | AIO, e.g., ES, pref. THF | Yes |
| | (2) 1-4 moles, pref. 3 moles, monoanion of XV (assuming 100% conversion of XV to its monoanion) per mole XIV. | −80°−−40° C., pref. −80°− −70° C. | 0.25-1.5 hrs. | Same as Step 1 | Yes |
| | (3) Quench with, for example, saturated ammonium chloride solution. | −80°-25° C. | 1-5 min. | — | — |
| F (Hydrolysis) | At least 2 moles, pref. 2-2.3 moles, XVII per mole XVI. | 0° C.-reflux, pref. 0°-75° C., esp. 20°-50° C. | 1-4 hrs. | Inert aqueous organic, e.g., mixture of water and lower alkanol, pref. mixture of water and methanol or, esp., ethanol | — |
| G (Wittig) | Alternative a: (1) 1-2 moles strong base, e.g., sodium hydride or pref. n-butyllithium, per mole XIX. Pref., slowly add n-butyllithium solution to solution of XIX. | −40°-5° C., pref. −35°− −20° C. | 5-60 min. | AIO, e.g., HC such as toluene or, pref., ES such as THF | Yes |
| | (2) 0.65-1.5 moles XXI per mole XIX used in Step 1. | −55°-25° C., pref. −35°− −5° C. | 0.75-18 hrs., pref. 1-4 hrs. | Same as Step 1 | Yes |
| | Alternative b: (1) 1-1.04 moles strong base, pref. n-butyllithium or lithium diisopropylamide, and, optionally, 1.75-2 moles lithium chloride per mole XX. Add strong base to other reactant(s). | −80°-0° C. | 0.2-1.5 hrs. | AIO, pref. ES, esp. THF | Yes |
| | (2) 1-1.2 moles XXI per mole XX used in Step 1 and after 10-20 min., optionally but pref., add 1-1.25 moles strong base, | −80°-25° C. | 1-12 hrs. | Same as Step 1 | Yes |

-continued

| Reaction/Type | Reagents, Molar Ratios and Comments | Temperature | Time | Solvent | Inert Atmosphere |
|---|---|---|---|---|---|
| | pref. lithium diisopropylamide.2THF complex, per mole XX used in Step 1. Pref., commence reaction at $-80°$ — $-30°$ C. and after 0.5-1 hr. allow to warm to $20°-25°$ C. | | | | |
| | (3) Quench with, e.g., ammonium chloride solution. Product (XXII) is a mixture of the (Z) and (E) (cis and trans, respectively) isomers which may be separated by chromatography. The (E) to (Z) ratio may be higher with Alternative b than with Alternative a. | $-10°-25°$ C. | 1-5 min. | — | — |
| H (Deprotection) | 2-15 moles, pref. 4-12 moles, fluoride reagent, esp. tetra-n-butylammonium fluoride or trihydrate thereof, per mole XXII and 0.8-2 moles, pref. 1-1.5 moles, glacial acetic acid per mole fluoride reagent. First add glacial acetic acid to solution XXII and then add fluoride reagent or add solution of XXII to solution of other reactants. | $20°-65°$ C. | 2-50 hrs. | AIO, e.g., ES, pref. THF, or acetonitrile | Yes |
| I (Hydrogenation) | Excess hydrogen (more than 1 mole per mole XXII) and catalytic amount of platinum dioxide (e.g., 1-5 g. per mole XXII). Initial hydrogen pressure is conveniently 30-60 p.s.i. | $20°-25°$ C. | Until 1 mole hydrogen per mole XXII is taken up | Lower alkanol, e.g., ethanol | — |
| J (Deprotection) | Same as Reaction H (Molar quantities are per mole XXII). | Same as H | Same as H | Same as H | Yes |
| K (Hydrolysis) | 1-1.3 equivalents XVII per mole XXXI or, if it is desired to isolate XXXII, 0.92-0.99 equivalent XVII per mole XXXI. | $0°$ C.-reflux, pref. $0°-75°$ C., esp. $20°-70°$ C. | 1-4 hrs. | Inert aqueous organic, e.g., mixture of water and lower alkanol, pref. mixture of water and methanol or, esp., ethanol | — |
| L (Acidification) | At least 1 equivalent, e.g., 1-1.25 equivalents, acid, e.g., 2N. hydrochloric acid, per mole XXXII. | $0°-25°$ C. | 1-5 min. | Water or mixture of water and water-miscible or partially miscible inert organic solvent, e.g., methanol, ethanol, diethyl ether or THF | — |
| M (Neutralization) | 0.95-0.99 equivalent, pref. 0.96-0.98 equivalent, XXXIV per mole XXXIII. | $0°-25°$ C., pref. $20°-25°$ C. | 2-10 min. | Same as Q | — |
| N (Lactonization) | Alternative a: Use of catalytic amount of strong acid such as p-toluenesulfonic acid. monohydrate is optional but usually omit. Use of Dean-Stark apparatus is pref. if solvent forms azeotrope with water. | $75°$ C.-reflux, pref. $75°-150°$ C., esp. $80°-120°$ C. | 3-18 hrs., pref. 4-7 hrs. | AIO, pref. HC, e.g., benzene, toluene or xylene or mixture thereof | — |
| | Alternative b: 1-1.5 moles of a lactonization agent, e.g., a carbodiimide, pref. a water-soluble carbodiimide such as N—cyclohexyl-N'—[2'-(N"—methylmorpholinium)-ethyl] carbodiimide p-toluenesulfonate, per mole XXXIII. Alternative b often results in higher yields of XXXVI than Alternative a. Racemic erythro XXXIII yields racemic trans (lactone) XXXVI, racemic threo XXXIII yields racemic cis (lactone) XXXVI, mixture of racemic erythro and threo XXXIII yield mixture of racemic trans and cis (lactones) XXXVI, and single enantiomer of XXXIII yields single enantiomer of XXXVI, e.g., 3R, 5S erythro XXXIII yields 4R, 6S trans XXXVI. | $10°-35°$ C., pref. $20°-25°$ C. | 2-8 hrs., pref. 3-4 hrs. | AIO, pref. HLA, esp. methylene chloride | — |
| O (Esterification) | At least 2 moles, e.g., 2-10 moles, pref. 2.05-2.5 moles, XXXVII per mole XXXVI. See comment concerning Reaction P, this column | $0°-70°$ C., pref. $20°-25°$ C. | 2-12 hrs. | IO, e.g., ES such as THF or alcohol of the formula $R_{19}$-OH | — |

-continued

| Reaction/Type | Reagents, Molar Ratios and Comments | Temperature | Time | Solvent | Inert Atmosphere |
|---|---|---|---|---|---|
| P (Hydrolysis) | 1–1.3 equivalents XVII per mole XXXVI or, if it is desired to isolate XXXII, 0.95–1 equivalent, preferably 0.97–0.99 equivalent, XVII per mole XXXVI.<br><br>Racemic trans (lactone) XXXVI yields racemic erythro XXXII or XXXVIII, racemic cis (lactone) XXXVI yields racemic threo XXXII or XXXVIII, mixture of racemic trans and cis (lactones) XXXVI yields mixture of racemic erythro and threo XXXII or XXXVIII, and single enantiomer of XXXVI yields single enantiomer of XXXII or XXXVIII, e.g., 4R, 6S trans XXXVI yields 3R, 5S erythro XXXII or XXXVIII. | 0° C.-reflux, pref. 0°–75° C. more pref. 20°–75° C., esp. 40°–60° C. | 1–6 hrs., pref. 1–4 hrs. | ($R_{19}$ same as in XXXVII), if a liquid Same as K | — |
| Q (Esterification) | 1–5 moles XXXIX and catalytic amount of acid, e.g., p-toluenesulfonic acid · monohydrate, per mole XXXIII. When reaction is run neat, use large excess of XXXIX, e.g., 50–100 moles, per mole XXXIII. | 20°–40° C. | 1–6 hrs. | AIO, e.g., ES such as THF or neat (if XXXIX is a liquid) | — |
| R (Oxidation) | (a) When $X_6$ is —CH=CH— or —CH$_2$—CH=CH—: 5–50 moles manganese dioxide (pref. activated) per mole LXVII.<br><br>(b) When $X_6$ is —(CH$_2$)$_n$— or —CH=CH—CH$_2$—:<br>(1) Preparation of Swern's Reagent: 0.9596 l. oxalyl chloride and 1.561 l. dimethyl sulfoxide per mole LXVII to be used in Step 2.<br>(2) Swern's Reagent from Step 1 and 6.969 l. triethylamine per mole LXVII. | 20°–80° C., pref. 40°–80° C.<br><br>−20°–0° C.<br><br>−60°––40° C., pref. −50° C. | 1–4 days<br><br>5–15 min.<br><br>1–6 hrs. | AIO, pref. ES or HC, esp. toluene<br><br>Neat<br><br>Methylene chloride | Yes<br><br>Yes<br><br>Yes |
| S (Hydrolysis) | Same as Reaction K | Same as K | Same as K | Same as K | — |
| T (Acidification) | Same as Reaction L | Same as L | Same as L | Same as L | — |
| U (Neutralization) | Same as Reaction M | Same as M | Same as M | Same as M | — |
| V (Esterification) | Same as Reaction Q (Molar quantities are per mole LXX) | Same as Q | Same as Q | Same as Q | — |
| AA (Reduction) | (1) 0.5–3.2 moles, pref. 0.75–3 moles, lithium aluminum hydride or 2–12 moles, pref. 3.5–12 moles, diisobutylaluminum hydride per mole XLI. Pref. commence reaction at −5°–5° C., allow reaction mixture to warm to 20°–25° C. as reaction proceeds and complete reaction at 20°–25° C.<br>(2) Quench with, for example, saturated ammonium chloride solution. | −5°–25° C., pref. −5°–5° C. →20°–25° C.<br><br>0–25° C. | 2–72 hrs., pref. 2–6 hrs. if ester group is not sterically hindered<br><br>1–5 min. | AIO, e.g., ES, pref. THF or diethyl ether<br><br>— | Yes<br><br>— |
| AB (Oxidation) | 1–3.5 moles, pref. 1.2–3 moles, pyridinium chlorochromate or pyridinium dichromate, 5–10 moles, pref. 6–8 moles, chromium trioxide (pref. complexed with pyridine, more pref. 2 moles pyridine per mole chromium trioxide), 5–50 moles, pref. 10–20 moles, manganese dioxide, pref. activated manganese dioxide, or, pref., 2–4 moles N—methylmorpholine-N—oxide.monohydrate and catalytic amount (e.g., 0.02–0.05 mole) tris(triphenylphosphine)ruthenium (II) chloride (CLI), per mole XLII. | 20°–120° C., with manganese dioxide and 20°–30° C., pref. 20°–25° C., with others | 2–18 hrs., pref. 3–12 hrs., with pyridinium chlorochromate or chromium trioxide, 8–24 hrs., pref. 15–18 hrs., with pyridinium dichromate, 4–48 hrs., pref. 10–24 hrs. with manganese dioxide and 1–5 hrs. with N—methylmorpholine-N—oxide.monohy- | AIO, pref. HLA, esp. methylene chloride, for pyridinium chlorochromate, chromium trioxide and pyridinium dichromate, pref. HLA, HC or ES, esp. toluene or diethyl ether, for manganese dioxide and dry acetone for N—methylmorpholine-N—oxide.monohydrate | Yes |

-continued

| Reaction/Type | Reagents, Molar Ratios and Comments | Temperature | Time | Solvent | Inert Atmosphere |
|---|---|---|---|---|---|
| AC (Wittig) | (1) Synthesis of ylide: 1–1.05 moles strong base, e.g., sodium hydride, phenyllithium or, pref., n-butyllithium per mole XLIV. Pref., slowly add solution of strong base to solution of XLIV. | −40°–0° C., pref. −35°– −20° C. | drate 1–4 hrs. | AIO, pref. ES, e.g., THF | Yes |
| | (2) Synthesis of enol ether: Ylide from 1–1.05 moles XLIV per mole XLIII. | −30°–0° C., pref. −20°–0° C. | 1–4 hrs. | Same as Step 1 | Yes |
| | (3) Hydrolysis of enol ether: Large molar excess, e.g., 2–20 moles, strong acid, e.g., 70% perchloric acid, per mole XLIII used in Step 2. | 0°–30° C. | 8–24 hrs. | Mixture of aqueous acid and ES, e.g., mixture of 70% perchloric acid and THF | — |
| AD (Wittig) | Same as Reaction AC (Molar quantities in Steps 2 and 3 are per mole XLV). | Same as AC | Same as AC | Same as AC | Same as AC |
| AE (Wittig) | Same as Reaction AC (Molar quantities in Steps 2 and 3 are per mole XLVI). | Same as AC | Same as AC | Same as AC | Same as AC |
| AF (Wittig) | Alternative a: 1–2 moles, pref. 1–1.7 moles, XLVIII per mole XLIII. | 80° C.-reflux, esp. refluxing toluene | 6–18 hrs. | AIO, pref. HC, esp. toluene | Yes |
| | Alternative b: (1) Synthesis of ylide: 0.99–1.07 moles strong base, pref. sodium hydride, per mole XLIX. Pref., add small amount of XLIX to suspension of sodium hydride in THF stirred at 20°–25° C., cool to −20°– −15° C. once reaction commences and complete reaction at −20°–−15° C. or run entire reaction at −10°–0° C. | −20°–25° C., pref. −20°–0° C. | 0.5–2 hrs. | AIO, pref. ES, esp. THF | Yes |
| | (2) 1–1.6 moles ylide from XLIX (assuming 100% conversion of XLIX to ylide) per mole XLIII. Pref., add solution of XLIII to ylide solution at −20°–0° C., stir at −20°–25° C. for a balance of reaction and if necessary, complete reaction at 40°–65° C. | −20°–65° C. | 0.75–20 hrs. | Same as Step 1 | Yes |
| | (3) Quench with, e.g., water. | 0°–25° C. | 1–5 min. | — | — |
| AG (Reduction) | (1) At least 2 equivalents transferable hydride from a metal hydride reducing agent, e.g., lithium aluminum hydride or diisobutylaluminum hydride, per mole L, pref. 3.8–6 moles diisobutylaluminum hydride per mole L. | −78°–25° C. | 0.7–18 hrs. | AIO, pref. ES, e.g., THF | Yes |
| | (2) Quench with, e.g., water or saturated ammonium chloride or sodium sulfate solution. | −78°–25° C. | 1–15 min. | — | — |
| AH (Oxidation) | 5–50 moles, pref. 10–30 moles, manganese dioxide, pref. activated manganese dioxide, or, pref., 2–4 moles N—methylmorpholine-N—oxide.monohydrate and catalytic amount (e.g., 0.02–0.05 mole) CLI, per mole LI. | 20° C.-reflux, pref. 20°–115° C. with manganese dioxide and 20°–25° C. with N—methyl-morpholine-N—oxide.monohydrate | 3–24 hrs. pref. 10–18 hrs. | AIO, pref. HC or ES, esp. toluene or diethyl ether, with manganese dioxide and dry acetone with N—methyl-morpholine-N—oxide.monohydrate | Yes with N—methyl-morpholine-N—oxide.monohydrate |
| AI | (p) Preparation of LIII: 2–2.1 moles, pref. 2 moles, t-butyllithium, pref. as 1–2M solution in pentane, per mole cis-1-bromo-2-ethoxyethylene. | −80°–−75° C., pref. −78° C. | 1–5 hrs., pref. 2–4 hrs. | AIO, e.g., ES, pref. THF | Yes |
| | (1) 1–1.75 moles LIII (assuming 100% yield from Step p) per mole XLIII. When it is desired to isolate and/or purify the crude enol ether intermediate, quench the reaction mixture with, e.g., saturated ammonium chloride solution at −80°–25° C. for 1–5 min. Otherwise, quenching is optional since it will occur at the beginning of Step 2. Crude enol ether product of this step may be used in next step without isolation and purification but isolation and purification of enol ether intermediate may improve yield of LII from next step. | −80°–−40° C., pref. −80°– −60° C. | 0.75–8 hrs., pref. 1–4 hrs. | Same as Step p | Yes |
| (Hydrolysis) | (2) Catalytic amount of p-toluenesulfonic | 20°–40° C., | 0.5–5 | Mixture of ES | — |

-continued

| Reaction/Type | Reagents, Molar Ratios and Comments | Temperature | Time | Solvent | Inert Atmosphere |
|---|---|---|---|---|---|
| | acid or monohydrate thereof (e.g., 0.5–100 g., pref. 1–5 g., per mole XLIII used in Step 1) and water. | pref. 20°–25° C. | hrs., pref. 0.5–4 hrs. | and water, pref. mixture of THF and water | |
| BA (Halogenation) | 1–4 moles LV or LVI, pref. 1.5–4 moles LV or 1.5–1.8 moles LVI, per mole XLII. | −10°–80° C. | 2–18 hrs. | AIO, pref. ES, e.g., diethyl ether or THF, HLA, e.g., methylene chloride, or HC, e.g., benzene | — |
| BB | Excess triphenylphosphine, e.g., 2–10 moles per mole LVII. | 60° C.-reflux, pref. ≦150° C., esp. 75°–78° C. (in absolute ethanol) | 0.5–24 hrs. | AIO, pref. absolute ethanol | Yes |
| BC | 1–1.1 moles LIX per mole LVII. Can use excess LIX as the solvent. | 20°–140° C., usually 110°–140° C. | 6–24 hrs., usually 10–18 hrs. | HC, e.g., benzene or xylene or neat (excess LIX is solvent) | Yes |
| BD | Same as Reaction B, Alternative a (Molar quantities are per mole XLV). | Same as B, a | Same as B, a | Same as B, a | Yes |
| BE (Halogenation) | Same as Reaction BA (Molar quantities are per mole LXI). | Same as BA | Same as BA | Same as BA | — |
| BF | Same as Reaction BB (Molar quantities are per mole LXII). | Same as BB | Same as BB | Same as BB | Yes |
| BG | Same as Reaction BC (Molar quantities are per mole LXII). | Same as BC | Same as BC | Same as BC | Yes |
| BH (Dehydrogenation) | 1–1.1 moles 2,3-dichloro-5,6-dicyano-1,4-benzoquinone (DDQ) per mole LXV. | 20°–30° C., pref. 20°–25° C. | 1–18 hrs. | AIO, pref. ES or HLA, esp. dioxane or methylene chloride | — |

In the preceding table,
AIO=anhydrous inert organic solvent
ES=ether solvent, for example, diethyl ether, 1,2-diethoxyethane, 1,2-dimethoxyethane, tetrahydrofuran and mixtures thereof
esp.=especially
HC=hydrocarbon solvent, for example, benzene, toluene, xylene and mixtures thereof
HLA=halogenated lower alkane solvent, for example, carbon tetrachloride, chloroform, 1,1-dichloroethane, 1,2-dichloroethane, methylene chloride and 1,1,2-trichloroethane, usually preferably methylene chloride
hr. (hrs.)=hour(s)
IO=inert organic solvent
min.=minutes
pref.=preferably, preferred
THF=tetrahydrofuran Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the art to vary those that are not critical.

The reaction times set forth in the preceding table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized. All solvent mixtures are by volume, unless otherwise indicated.

The term "inert atmosphere", as utilized in the preceding table, means an atmosphere that does not react with any of the reactants, intermediates or end products or otherwise interfere with the reaction. While a carbon dioxide atmosphere is suitable for certain reactions, the inert atmosphere is usually nitrogen, helium, neon, argon or krypton, or a mixture thereof, and most often dry nitrogen to maintain anhydrous conditions. Most reactions, including those where the use of an inert atmosphere is not specified, are carried out under an inert atmosphere, usually dry nitrogen or argon, for convenience.

In the preceding table, n-butyllithium is preferably employed as a 1.3–1.7 M. solution in hexane, and lithium diisopropylamide is preferably prepared in situ from n-butyllithium and diisopropylamine.

Reactions analogous to many of the reactions of this specification are described in detail in U.S. Pat. Nos. 4,613,610, 4,668,794 and 4,686,237 and World (P.C.T.) Published Application Nos.84/02131 and 86/07054. These reactions may be carried out analogously to the corresponding reactions of said patents and applications. Said patents and applications are hereby incorporated by reference. Generally, where the reaction conditions set forth in said patents and applications differ from those set forth in this specification, the reaction conditions set forth in said patents and applications may also be utilized for the compounds of this specification.

The product of each reaction may, if desired, be purified by conventional techniques such as recrystallization (if a solid), column chromatography, preparative thin layer chromatography, gas chromatography (if sufficiently volatile), fractional distillation under high vacuum (if sufficiently volatile) or high pressure (performance) liquid chromatography (HPLC). Often, however, the crude product of one reaction may be employed in the following reaction without purification.

Some of the reactions described above may yield mixtures of two or more products only one of which leads to the desired compound of Formula I. Any obtained mixture may be separated by conventional techniques such as those set forth in the preceding paragraph.

As is evident to those in the art, each of the compounds of Formulae I wherein Z is a group of Formula c (including those of Formulae LXVIII–LXXII), VIII, XI, XIV and LXV and has a single center of asymmetry and, therefore, may be resolved into two optically active isomers. When a compound of Formula VIII or XIV is converted into a compound of Formula IX or XVI, respectively, an additional center of asymmetry is generated. Consequently, when a racemic compound of Formula VIII or XIV is utilized, four stereoisomers (two pairs of diastereoisomers) of the resulting compound of Formula IX or XVI are formed, whereas when an optically pure compound of Formula VIII or XIV is utilized, two diastereoisomers of the compound of Formula IX or XVI are formed.

The compounds of Formulae I wherein Z is a group of Formula a or b (including those of Formulae IX, XVIII, XXIII, XXV, etc.), XVI, XXI, XXII and XXIV have two centers of asymmetry and, therefore, may exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one center of asymmetry) or four (if formed from a racemic compound having one center of asymmetry) stereoisomers.

The center of asymmetry of each compound of Formula LXV may be ignored since it is destroyed in the following reaction (Reaction BH).

The obtained mixtures of stereoisomers may be separated by conventional means. For example, diastereoisomers may be separated by fractional crystallization, column chromatography, preparative thin layer chromatography and HPLC. Each mixture of four stereoisomers of a compound of Formula XXXVI may, for example, be separated by HPLC into its cis and trans (lactone) components, each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and/or HPLC. For example, a racemic lactone of Formula XXXVI may be reacted with an excess of R-(+)-α-methylbenzylamine (or the corresponding S-(−) compound) to form a mixture of two diastereoisomeric α-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°–25° C. for 16–24 hours. The reaction is run neat, with the excess amine serving as the solvent. After the reaction, the excess amine is removed by vacuum distillation at 25°–35° C. After separation, each chiral amide may be hydrolyzed to the corresponding, for example, sodium, salt by, for example, refluxing with 1.5–3, preferably 2–2.2, equivalents of a base such as sodium hydroxide for 5–25 hours in a mixture of water and ethanol. The resulting salts may be converted to the corresponding free acids, esters, lactones and other salts by conventional means such as the reactions set forth in Reaction Scheme III. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, e.g., (−)-α-naphthylphenylmethylchlorosilane (Sommer et al., J. Am.

Chem. Soc. 80, 3271 (1958).), to form a mixture of two diastereoisomeric silyloxy compounds, which mixture may be separated by conventional techniques. For example, diastereoisomeric (−)-α-naphthylphenylmethylsilyl derivatives of a lactone of Formula XXXVI may be separated on a silica column having covalently bound L-phenylglycine. After separation, the optically pure salts, amides, esters or silyloxy compounds are reconverted to the corresponding carboxy group- or hydroxy group-containing compounds with retention of optical purity. For example, the process conditions disclosed for Reactions H and J may be utilized to cleave (−)-α-naphthylphenylmethylsilyl and other silyl groups.

The compounds of Formulae VII, X, XII, XIII, XV, XVII, XXI, XXXIV, XXXVII, XXXIX, XLIV, XLVIII, XLIX, LIII, LV, LVI, LIX and LXV and the reagents not designated by a Roman numeral are known or, if unknown, may be synthesized by processes analogous to those described in the literature for similar known compounds.

For example, the compounds of Formula XXI and the synthesis thereof are disclosed in U.S. Pat. No. 4,613,610. Said patent, particularly columns 19-24, 27-30 and 41-48 thereof, is hereby incorporated by reference. Furthermore, a preferred process for the synthesis of the erythro racemate of the compound of Formula XXI wherein $R_{17}$ is hydrogen, $R'_{19}$ is methyl, and $X_3$ is a direct bond is disclosed in Kapa, Tetrahedron Letters 25, 2435-2438 (1984). The other compounds of Formula XXI wherein $R_{17}$ is hydrogen, and $X_3$ is a direct bond in racemic erythro form may be synthesized similarly. See also U.S. Pat. No. 4,571,428. Said patent, particularly columns 3-11 thereof, is hereby incorporated by reference. A particularly preferred process for the synthesis of the 3R,5S enantiomers of the compounds of Formula XXI wherein $R_{17}$ is hydrogen, and $X_3$ is a direct bond is disclosed in copending application Ser. No. 07/023,079, filed on Mar. 6, 1987 by Kau-Ming Chen, Goetz E. Hardtman, Prasad K. Kapa, George T. Lee, Jerome Linder and Sompong Wattanasin and now abandoned.

The compounds of Formula LXV are also either known or, if unknown, may be synthesized by processes analogous to those described in the literature for the known comounds of said formula and similar compounds. See, for example, British patent application No. 2,128,186 and European patent application No. 114,273, which are hereby incorporated by reference.

Since any compound of Formula I wherein Z is a group of Formula a or c wherein $R_{18}$ is a cation other than M may be converted into the corresponding compound wherein $R_{18}$ is hydrogen, M or $R_{19}$ by the processes of Reaction Schemes III and IV, the compounds of Formula I wherein Z is a group of Formula a or c and $R_{18}$ is a pharmaceutically unacceptable cation are also within the scope of this invention since they are useful as intermediates. However, such compounds are not compounds of Formula I as utilized in this specification, except where indicated to the contrary.

Also within the scope of this invention are the intermediates of Formulae VIII, XI, XIV, XVI, XIX, XX, XXII, XXIV, XLI-XLIII, XLV-XLVII, L-LII, LVII, LXI and LXII. The preferences for each variable are the same as those set forth for the compounds of Formula I, with the preferred groups of such compounds including those that correspond to Groups (i)-(v), (xv)-(xix), (xxix)-(xxxiii) and (xliii)-(lvii).

Besides having the utility set forth below, every compound of Formula I is useful as an intermediate in the synthesis of one or more other compounds of Formula I utilizing the reactions set forth in Reaction Schemes III and IV.

The compounds of Formula I exhibit pharmacological activity and are, therefore, useful as pharmaceuticals.

In particular, the compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. The biological activity of the compounds of Formula I may be demonstrated in the following two tests:

Test A. In Vitro Microsomal Assay of HMG-CoA Reductase Inhibition:

This test is carried out precisely as described in column 53 of U.S. Pat. No. 4,613,610 and on page 30 of World (PCT) Published patent application No. 84/02131, both of which are hereby incorporated by reference as if set forth herein in their entirety. The concentration of the test substance (compound of Formula I) in the assay system is 0.001-2,000 μmolar. The obtained $IC_{50}$ is the concentration of the test substance in the assay system observed or calculated to produce a 50% inhibition of HMG-CoA reductase activity.

Test B. In Vivo Cholesterol Biosynthesis Inhibition Test:

This test is carried out precisely as described in column 53 of said U.S. Pat. No. 4,613,610 and on page 33 of said World (PCT) Published Patent Application No. 84/02131, both of which are hereby incorporated by reference as if set forth herein in their entirety. In this test the rats are orally administered the test substance (compound of Formula I) at a dose of 0.1-200 mg/kg. body weight. The obtained $ED_{50}$ is the dose of the test substance observed or calculated to produce a 50% inhibition of 3β-hydroxysterol synthesis.

The compounds of Formula I including those of each subgroup thereof) are, therefore, useful for lowering the blood cholesterol level in animals, e.g., mammals, especially larger primates such as humans, and, therefore, as hypolipoproteinemic and anti-atherosclerotic agents.

The precise dosage of the compound of Formula I to be employed for inhibiting cholesterol biosynthesis and the treatment of atherosclerosis depends upon several factors including the host, the nature and the severity of the condition being treated, the mode of administration and the particular active substance (compound of Formula I) employed. However, in general, satisfactory results in animals are indicated to be obtained at daily dosages from about 0.05 mg./kg. to about 200 mg./kg. For larger mammals such as humans, an indicated daily dosage is in the range of about 2.5 mg. to about 2,000 mg. of a compound of Formula I conveniently administered once a day or in divided doses two to four times a day.

The compounds of Formula I may be administered by any conventional route, in particular enterally, preferably orally, e.g., in the form of tablets or capsules, or parenterally, e.g., in the form of sterile injectable solutions or suspensions.

The compound of Example 2 is the preferred compound. It has, for example, been determined that, in Test A, this compound has an $IC_{50}$ of 0.01 μmolar as compared to an $IC_{50}$ of 1.01 μmolar for Compactin and an $IC_{50}$ of 0.14 μmolar for Mevinolin and, in Test B, this compound has an $ED_{50}$ of 0.05 mg./kg. as compared to an $ED_{50}$ of 3.5 mg./kg. for Compactin and an $ED_{50}$ of 0.38 mg./kg. for Mevinolin. It is, therefore, indicated that, for this use, the compound of Example 2 may be administered to larger mammals, e.g., humans, by similar modes of administration at dosages significantly lower than those conventionally employed with Compactin and Mevinolin (e.g., 20–80 mg./day orally of Mevinolin).

The compounds of Formula I may be formulated into pharmaceutical compositions comprising a compound of Formula I and at least one pharmaceutical solid or liquid carrier (or diluent). Such compositions may be manufactured in conventional manner. The compounds of each subgroup thereof may likewise be formulated into such pharmaceutical compositions.

The compounds of Formula I (including those of each subgroup thereof) may be formulated into such pharmaceutical compositions containing an amount of the active substance that is effective for inhibiting cholesterol biosynthesis and treating atherosclerosis in unit dosage form and such compositions comprising at least one solid pharmaceutically acceptable carrier. Unit dosage forms contain, for example, from about 0.6 mg. to about 500 mg. of a compound of Formula I.

The following examples show representative compounds encompassed by this invention and their synthesis. However, it should be understood that they are for purposes of illustration only.

EXAMPLE A 1,1-Dimethylethyl
(3R,5S)-3,5-di-[(1',1'-dimethylethyl)-diphenylsilyloxy]-6-oxohexanoate

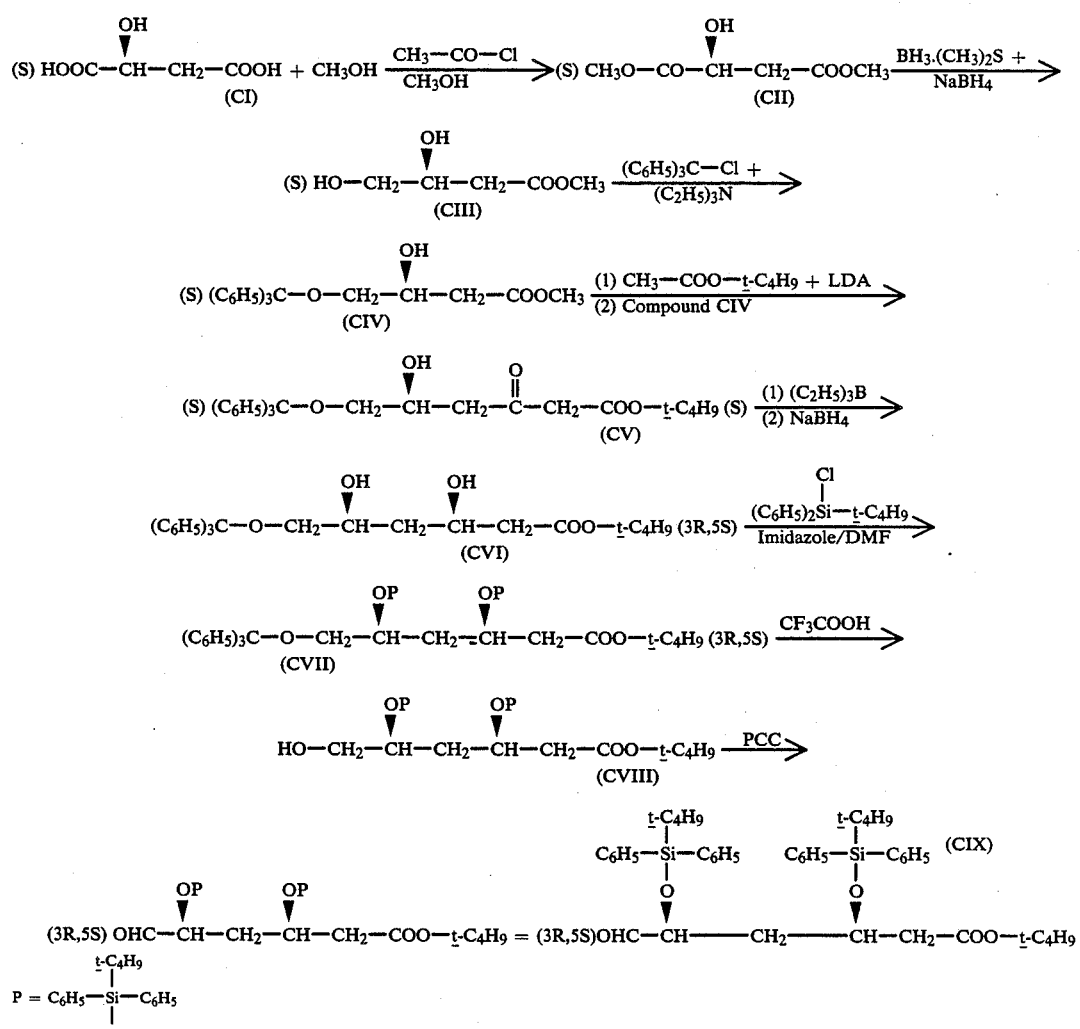

Step 1

Dimethyl (S)-hydroxybutanedioate (Compound CII)

(a) 750 g. (9.6 moles) of acetyl chloride is added over a period of 30 minutes to 13.5 of methanol sitrred at −5°–0° C. while maintaining an internal temperature of 0°–2° C. (the addition being very exothermic), the reaction mixture is stirred at 0° C. for 1 hour, 1.76 kg. (13.1 moles) of (S)-hydroxybutanedioic acid is added over a period of 30 minutes while maintaining an internal temperature of 0°–2° C. (the addition being slightly exothermic), and the reaction mixture is stirred at 0°–2° C. for 2 hours and at 20°–25° C. for 16 hours, the reaction mixture being stirred under nitrogen throughout. 898 g. (8.47 moles) of anhydrous sodium carbonate is added over a period of 15 minutes while maintaining an internal temperature of 20°–25° C. to adjust the pH to 7–8 (the addition being slightly exothermic), and the reaction mixture is stirred at 20°–25° C. for 30 minutes and filtered. The filter cake is washed twice with 500 ml. portions of methanol, the filtrate and washings are combined, and the solution is evaporated at 25–30 mm. Hg while maintaining an internal temperature of 35°–40° C. to a volume of about 2.5 l. and filtered. The filter cake is washed with 500 ml. of methanol, the filtrate and washing are combined, and the solvent is distilled at 25–35 mm. Hg and an internal temperature of 40° C. to obtain the crude product (2.22 kg.).

(b) A solution of 300 g. of crude product from Part (a) of this step in 300 ml. of methylene chloride is added to a slurry of 300 g. of 70–230 mesh ASTM silica gel in 1.4 l. of methylene chloride, and the product is eluted with 7–8 l. of methylene chloride. The methylene chloride is distilled at 30–40 mm. Hg and an external temperature of 50° C. to obtain the partially purified product which is vacuum distilled at 0.6 mm. Hg and an internal temperature of 96°–98° C. to obtain the 96.7% pure product (239 g.). B.p. 90°–92° C./1.5–2 mm. Hg, 78°–80° C./0.6 mm. Hg.

(c) The remainder of the crude product is similarly purified.

Step 2

Methyl (S)-3,4-dihydroxybutanoate (Compound CIII)

7.5 g. (0.2 mole) of sodium borohydride is added in one portion to a mixture of 523 ml. of 10M. boranedimethylsulfide complex (5.23 moles borane) and 1.8 l. of dry tetrahydrofuran stirred at 20°–25° C., the reaction mixture is stirred at 20°–25° C. for 30 minutes, a solution of 744 g. of 94% pure Compound CII (4.31 moles) in 1.2 l. of dry tetrahydrofuran is added over a period of 1 hour while maintaining with external cooling at 3°–5° C. an internal temperature of 20°–25° C. (the reaction is very exothermic, and hydrogen is evolved), and, after the exotherm stops, the reaction mixture is stirred at 20°–25° C. for 1 hour and cooled to 20° C., the reaction mixture being stirred under nitrogen throughout. 1.8 l. of methanol is slowly added while maintaining an internal temperature of 20°–25° C. (The first third of the addition is very exothermic and foaming occurs.) The reaction mixture is stirred for 30 minutes while maintaining an internal temperature of 20°–25° C., the solvent is distilled at 20–30 mm. Hg and an external temperature of 40°–45° C., 500 ml. of toluene is added, the solvent is distilled at 20–30 mm. Hg and an external temperature of 40°–45° C., an additional 500 ml. of toluene is added, and the solvent is distilled at 20–30 mm. Hg and an external temperature of 40°–45° C. to obtain the crude (89.7% pure) product as a very thick stirrable oil (633 g.). The entire reaction and the solvent distillations must be vented through bleach to trap any escaping dimethylsulfide.

Step 3

Methyl (S)-3-hydroxy-4-(triphenylmethoxy)butanoate (Compound CIV)

(a) A solution of 1.82 kg. (6.53 moles) of triphenylmethyl chloride in 2.5 l. of methylene chloride is added over a period of 12 minutes to a mixture of 716 g. of 81.7% pure Compound CIII (4.40 moles), 880 g. (8.7 moles) of triethylamine and 4.9 l. of methylene chloride stirred at 15° C. while maintaining an internal temperature of 15°–20° C. (the addition being exothermic), and the reaction mixture is stirred at 23° C. for 16 hours, stirred at an internal temperature of 38°–40° C. for 15 minutes (during which gas evolves) and cooled to 25° C., the reaction mixture being maintained under nitrogen throughout. 7.4 l. of water is added, the bottom organic layer is separated, the aqueous layer is extracted with 500 ml. of methylene chloride, the methylene chloride extract is combined with the bottom organic layer, and the combined organic layers are washed successively with 7.4 l. of water, 7.4 l. of saturated sodium bicarbonate solution and 3.7 l. of water and filtered to remove any insolubles. The solvent is distilled at 20–30 mm. Hg and a maximum external temperature of 50°–60° C. to obtain a thick dark stirrable oil. 2.5 l. of methanol is added with stirring at 50° C., and the mixture is stirred at 50° C. for 5 minutes, cooled to 20° C. and filtered. The filter cake is washed with 1 l. of methanol, the filtrate and washing are combined, and the solvent is distilled at 20–30 mm. Hg and an external temperature of about 50° C. to obtain the crude product as a thick stirrable brown oil (1.75 kg.).

(b) A 90 cm.×13 cm. chromatographic column is charged with 7.2 l. of 1:2 ethyl acetate/mixed hexanes, 450 g. of sea sand is added, a slurry of 4 kg. of 70–230 mesh ASTM silica gel in 12 l. of 1:2 ethyl acetate/mixed hexanes is added while draining some of the solvent from the bottom of the column, sufficient solvent to lower the liquid level to the top of the silica gel is drained from the column, a solution of 1.0 kg. of the crude product of Part (a) of this step in 1.0 l. of methylene chloride is added, sufficient solvent to lower the liquid level to the top of the silica gel is drained from the column, the column is eluted with 18 l. of 1:2 ethyl acetate/mixed hexanes to obtain six fractions, and the column is eluted with 12 l. of 1:1 ethyl acetate/mixed hexanes to obtain eight fractions containing relatively pure product. These eight fractions are combined, the solvent is distilled at 20–30 mm. Hg and 60° C. to obtain a thick stirrable oil, 1 l. of isopropanol is added, the solvent is distilled at 20–30 mm. Hg and a maximum internal temperature of 60° C., an additional 1 l. of isopropanol is added, the solvent is distilled at 20–30 mm. Hg and a maximum internal temperature of 60° C., and the residue is added to 2 l. of isopropanol. The resulting solution is cooled to 0°–5° C. and maintained at this temperature for 3–4 hours. The solid is collected by filtration, washed twice with 250 ml. portions of cold (0°–5° C.) isopropanol and vacuum dried at 50°–60° C. to constant weight to obtain the 94.9% pure product (473 g.), m.p. 80°–82° C., $[\alpha]_{589}{}^{25} = -5.52°$ (c=1.5580, $CH_2Cl_2$). All chromatography fractions and mother liquors containing impure product may be combined and rechromatographed, etc. to obtain additional product.

(c) The balance of the crude product is similarly purified.

Step 4

1,1-Dimethylethyl
(S)-5-hydroxy-3-oxo-6-(triphenylmethoxy)hexanoate
(Compound CV)

1.98 l. of 1.6M. n-butyllithium/hexane (3.17 moles) is added over a 30 minute period to a mixture of 321 g. (3.17 moles) of diisopropylamine and 1.5 l. of dry tetrahydrofuran stirred at −50°––40° C. during which the internal temperature rises to −5°-0° C., the pale yellow solution is stirred at −5°-0° C. for 30 minutes and cooled to −65° C., 367 g. (3.16 moles) of t-butyl acetate is added over a period of 40 minutes while maintaining an internal temperature of −63°––60° C. (the addition being exothermic), the reaction mixture is stirred at −62°––60° C. for 40 minutes, a solution of 300 g. (0.80 mole) of 95+% pure Compound CIV in 1.35 l. of dry tetrahydrofuran is added over a period of 25 minutes while maintaining an internal temperature of −62°––58° C. (the addition being exothermic), and the reaction mixture is stirred at −62°––58° C. for 1 hour, warmed to −5°-0° C. over a period of 45 minutes and stirred at −5°-0° C. for 30 minutes, the reaction mixture being stirred under nitrogen throughout. 1.8 l. of saturated ammonium chloride solution is added over a period of 3 minutes while maintaining an internal temperature of below 15° C. (the addition being exothermic), the mixture is stirred at 10°–15° C. for 10 minutes, 2.1 l. of toluene is added, and the top organic layer is separated, washed three times with 1.5 l. portions of water and, if any insolubles are present, filtered The solvent is distilled at 20–30 mm. Hg and an internal temperature of 50°–60° C. to obtain the crude (87.1% pure) product as a very thick yellow oil that is stirrable at 50° C. (415 g.).

Step 5

1,1-Dimethylethyl
(3R,5S)-3,5-dihydroxy-6-(triphenylmethoxy)hexanoate
(Compound CVI)

A mixture of 715 ml. of 1M. triethylborane/tetrahydrofuran (715 mmoles), 4.76 l. of dry tetrahydrofuran and 1.44 l. of methanol is stirred at 18°–22° C. for 45 minutes and cooled to −75° C., a solution of 254.4 g. of crude (90% pure) Compound CV (0.497 mole) in 960 ml. of dry tetrahydrofuran is added over a period of 15 minutes while maintaining an internal temperature of −75°––72° C., the reaction mixture is stirred at −76°––75° C. for 1 hour, 24.96 g. (0.66 mole) of sodium borohydride is added in portions over a period of 15 minutes while maintaining an internal temperature of −76°––72° C., and the reaction mixture is stirred at −77°––76° C. for 4.5 hours, the reaction mixture being stirred under nitrogen throughout. 756 ml. of saturated ammonium chloride solution is slowly added over a period of 25 minutes while maintaining an internal temperature of −76°––67° C. (the addition is exothermic, and some foaming occurs), the mixture is stirred at −68°––67° C. for 30 minutes and warmed to 10°–15° C. over a period of 30 minutes, 360 ml. of water is added, the mixture is extracted with 3.6 l. of ethyl acetate, the top organic layer is separated and washed successively with 750 ml. of a 1:1 mixture of water and saturated sodium chloride solution and 750 ml. of saturated sodium chloride solution, and the solvent is distilled at 20–30 mm. Hg and a maximum external temperature of 50° C. 180 ml. of ethyl acetate is added, the solvent is distilled at 20–30 mm. Hg and a maximum external temperature of 50° C., and these two steps are repeated once. 2.91 l. of ethyl acetate is added to the obtained thick oil (the cyclic boronate), 290 ml. of 30% hydrogen peroxide solution (2.84 moles) is slowly added over a period of 20–30 minutes while maintaining an internal temperature of 20°–25° C. (the addition initially being exothermic), and the reaction mixture is stirred at 20°–25° C. for 2.5 hours and added to 360 ml. of water. The top organic layer is separated, washed three times (for 10–15 minutes each time) with 480 ml. portions of cold (0°–5° C.) 10% sodium sulfite solution (until the organic layer is free of peroxide) while maintaining an internal temperature of 25° C. and washed successively with 480 ml. of saturated sodium bicarbonate solution, 480 ml. of water (any emulsion that forms will separate within about an hour) and 480 ml. of saturated sodium chloride solution. The top organic layer is separated, and the solvent is distilled at 20–30 mm. Hg and a maximum external temperature of 50°–60° C. 326 ml. of methanol is added, the solvent is distilled at 20–25 mm. Hg and an internal temperature of 50°–60° C., and these two steps are repeated four more times. 100 ml. of toluene is added, the solvent is distilled at 20–30 mm. Hg and an internal temperature of 60° C., and these two steps are repeated three more times. The obtained oil is heated for an additional 3–4 hours at 20–30 mm. Hg and 50°–60° C. to obtain the crude (66.8% pure) product (255 g.). (The ratio of the 3R,5S isomer to the 3S,5S isomer is about 69:1 although in other batches it was as low as about 23:1.)

Step 6

1,1-Dimethylethyl
(3R,5S)-3,5-di-[(1',1'-dimethylethyl)-diphenylsilyloxy]-6-(triphenylmethoxy)hexanoate
(Compound CVII)

132.5 g. (1.95 moles) of imidazole is added to a mixture of 267 g. of crude (55.8% pure) Compound CVI (0.322 mole) and 900 ml. of N,N-dimethylformamide while maintaining an internal temperature of 23°–25° C., the mixture is heated to 70°–72° C., 235.8 g. (0.86 mole) of t-butyldiphenylchlorosilane is added over a period of 2 minutes, and the reaction mixture is stirred at 70°-72° C. for 18 hours and cooled to 10° C., the reaction mixture being stirred under nitrogen throughout. The reaction mixture is added to a mixture of 2.5 l. of hexane and 1.1 l. of water, the mixture is stirred for 5 minutes, the organic top layer is separated and washed twice with 1.1 l. portions of water, and the solvent is distilled at 20-30 mm. Hg and an external temperature of 40°-60° C. to obtain the crude (62.8% pure) product (437.7 g.).

Step 7

1,1-Dimethylethyl (3R,5S)-3,5-di-[(1',1'-dimethylethyl)-diphenylsilyloxy]-6-hydroxyhexanoate (Compound CVIII)

(a) A cold solution prepared from 960 g. of water, 600 g. of ice and 740 g. (6.49 moles) of trifluoroacetic acid is added over a period of 2 minutes to a solution of 432 g. of crude (62.8% pure) Compound CVII (0.29 mole) in 3.4 l. of methylene chloride while maintaining a maximum internal temperature of 25° C., and the reaction mixture is stirred at 22°-26° C. for 2.5 hours, the reaction mixture being stirred under nitrogen throughout. The organic bottom layer is separated and washed successively with 1.1 l. of saturated sodium bicarbonate solution and 1.0 l. of water, and th solvent is distilled at 20-30 mm. Hg and a maximum external temperature of 60° C. 100 ml. of mixed hexanes is added to the residue, the solvent is distilled at 20-30 mm. Hg and a maximum internal temperature of 60° C., and these two steps are repeated once, the distillation being continued until no more solvent distills off. 1.1 l. of mixed hexanes is added to the obtained thick semi-solid, the mixture is heated at 40°-45° C. for 10-15 minutes, cooled to 0°-5° C. and maintained at 0°-5° C. for 10 minutes, and the solid is collected by filtration and washed twice with 100 ml. portions of cold (10° C.) mixed hexanes. The filtrate and hexane washings are combined, and the solvent is distilled at 20-30 mm. Hg and an external temperature of 40°-60° C. to obtain the crude product as an oil (330 g.).

(b) The crude product of Part (a) is purified by HPLC using a Kiloprep 250 Millipore Process HPLC system with a reverse phase Kiloprep 250 $C_{18}$ cartridge (80 microns) and a 200 nm. detector. The column is flashed with methylene chloride until it is decontaminated (as indicated by the UV detector) and flushed with methanol for about 10 minutes and then with 9:1 methanol/water for about 6 minutes at a flow rate of 0.5 l/min. A solution of the crude product of Part (a) of this step in a mixture of 393 ml. of methanol and 22 ml. of water is placed on the column, and the column is eluted with 9:1 methanol/water for about 22 minutes, 11 minutes and 3 minutes to obtain fractions 1-3 and with methanol for about 4 minutes and 7 minutes to obtain fractions 4 and 5, the flow rate being 0.5 l./min. Fractions 4 and 5 are combined, the solvent is distilled at 20-40 mm. Hg and a maximum internal temperature of 40° C., 250 ml. of methylene chloride is added to the residue, the mixture is stirred at 30° C. for 5 minutes, the organic bottom layer is separated, and the solvent is distilled at 20-30 mm. Hg and a maximum internal temperature of 40°-45° C. 100 ml. of n-heptane is added, the solvent is distilled at 20-30 mm. Hg and 40°-45° C., and these two steps are repeated once. 460 ml. of n-heptane is added to the residue, and the mixture is heated to 80°-90° C. to dissolve the oil, allowed to cool to 20°-25° C. with stirring until solid forms and maintained at 10° C. for 2-3 hours. The resulting white solid is collected by filtration, washed twice with 50 ml. portions of cold (10° C.) n-heptane and vacuum dried to constant weight at 50° C. for 15 hours to obtain the 95.5% pure product as a white solid (122 g.). m.p. 79°-80° C., $[\alpha]_{589}^{20} = +8.35°$ (c=5.0, $CH_2Cl_2$). (The ratio of the 3R,5S isomer to the 3S,5S isomer is about 76:1.)

Step 8

1,1-Dimethylethyl (3R,5S)-3,5-di-[(1',1'-dimethylethyl)-diphenylsilyloxy]-6-oxohexanoate (Compound CIX)

150 g. (0.70 mole) of pyridinium chlorochromate is added over a period of 3 minutes to a mixture of 200 g. (0.28 mole) of 96.6% pure Compound CVIII, 2 l. of methylene chloride and 400 g. of 4 Å. powdered molecular sieves stirred at 20° C. while maintaining an internal temperature of 20°-22° C. (the addition being slightly exothermic), and the reaction mixture is vigorously stirred for 1 hour at 22°-25° C., the reaction mixture being stirred under nitrogen throughout. 3.32 l. of n-heptane is added, and the mixture is stirred at 23° C. for 5 minutes and filtered through 250 g. of Celite ® filter aid pre-wet witn n-heptane. The filter cake is washed twice with 200 ml. portions of n-hepthane, the filtrate and the n-heptane washings are combined, and the solvent is distilled at 20-30 mm. Hg and a maximum external temperature of 45°-50° C. 100 ml. of n-heptane is added, the solvent is distilled at 20-30 mm. Hg and a maximum external temperature of 45°-50° C., and this is repeated once. The resulting oil is dissolved in 400 ml. of 1:12 ethyl acetate/mixed hexanes and chromatographed on 420 g. of 70-230 mesh ASTM silica gel topped with about 2.5 cm. of sea sand utilizing a column having a 7 cm. inside diameter and 4 l. of 1:12 ethyl acetate/mixed hexanes as the eluant. The solvent is distilled at 20-30 mm. Hg and an external temperature of 50°-55° C. 100 ml. of n-heptane is added, the solvent is distilled at 20-30 mm. Hg and an external temperature of 50°-55° C., this is repeated once, and the residue is maintained at this pressure and temperature for 2 hours. 335 ml. of mixed hexanes is added at 40°-50° C. to the obtained thick oil, and the mixture is cooled to $-35°--30°$ C., seeded and maintained at $-35°--30°$ C. for 1 hour. The resulting white solid is collected by filtration, washed twice with 50 ml. portions of cold ($-25°--20°$ C.) mixed hexanes and dried to constant weight at 20-30 mm. Hg and 45°-50° C. for 24 hours to obtain the 99% pure product (175.2 g.), m.p. 81°-82° C., $[\alpha]_{589}^{25} = +5.21°$ (c=5.0, $CH_2Cl_2$). (The ratio of the 3R,5S isomer to the 3S,5R isomer is about 99:1.)

The stereochemistry of the compound may also be designated as R[R*,S*].

EXAMPLE 1
1,1-Dimethylethyl (3R,5S)-(E)-3,5-dihydroxy-7-[1',3'-dimethyl-4'-(4''-fluorophenyl)-6'-(1''-methylethyl)-1H-pyrazolo-[3,4-b]pyrid-5'-yl]hept-6-enoate
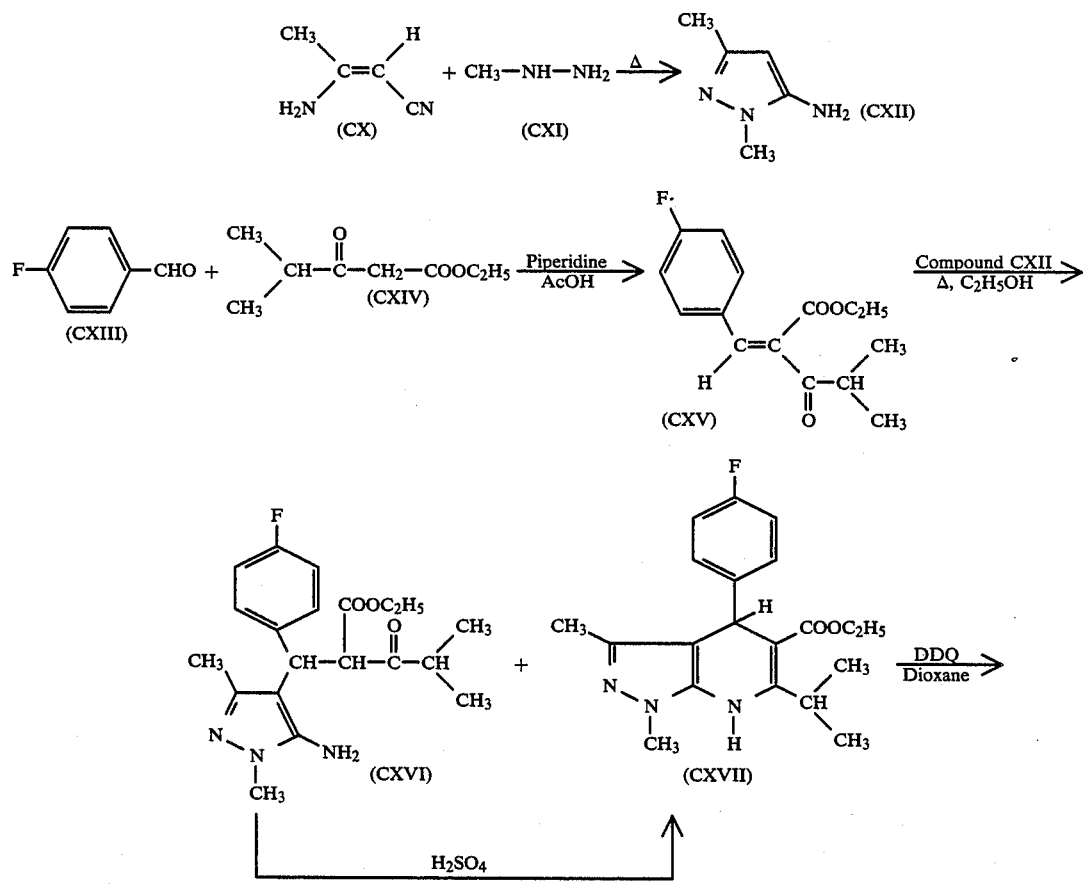

-continued

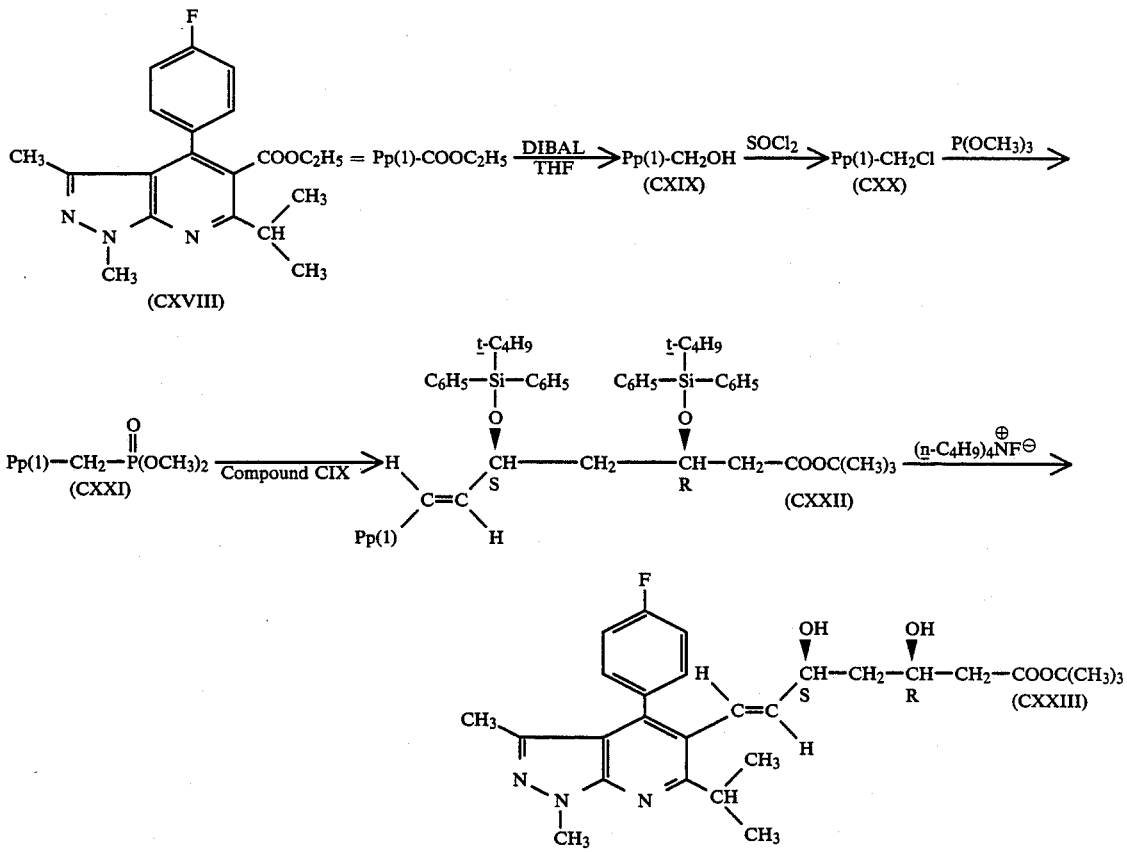

Step 1
5-Amino-1,3-dimethylpyrazole (Compound CXII)

A mixture of 250 g. (3.04 moles) of 3-aminocrotonitrile, 152.5 g. (3.3 moles) of methylhydrazine and 1 l. of absolute ethanol is refluxed for 8 hours (until the evolution of ammonia ceases) and cooled to 20°–25° C. The ethanol is evaporated at reduced pressure, and the residual oil is triturated with ~300 ml. of benzene. The resulting yellow-orange solid product is collected by filtration and vacuum dried at 45° C. to obtain the product (240 g. (71%)), m.p. 74°–76° C.

Step 2
Ethyl (Z)-2-[(4'-fluorophenyl)methylene]-4-methyl-3-oxopentanoate (Compound CXV)

A mixture of 981 g. (6.204 moles) of ethyl 4-methyl-3-oxopentanoate, 655 g. (6.204 moles) of 4-fluorobenzaldehyde, 80 ml. of glacial acetic acid, 80 ml. of dry piperidine and 2 l. of benzene is refluxed for 7–8 hours using a Dean-Stark apparatus to collect 105 ml. of water, cooled to 20°–25° C. and poured into 4 l. of cold water. 950 ml. of diethyl ether is added, the mixture is stirred for 5 minutes, the organic layer is separated, the aqueous layer is extracted with 950 ml. of diethyl ether, and the organic phases are combined, washed successively with 1 l. of 2N. sodium hydroxide solution, 1 l. of saturated sodium bisulfite solution and then water until neutral to pH paper, dried over anhydrous magnesium sulfate, filtered and evaporated at reduced pressure to obtain an orange-yellow oil which is fractionally vacuum distilled to obtain the product as an oil (1.29 kg.). B.p. 135°–145° C./0.7–1.4 mm. Hg, 133°–138° C./0.3–0.4 mm. Hg.

Step 3
Ethyl 3-(5'-amino-1',3'-dimethyl-1H-pyrazol-4'-yl)-3-(4'-fluorophenyl)-2-(2'-methyl-1'-oxopropyl)propanoate (Compound CXVI) and ethyl 4,7-dihydro-1,3-dimethyl-4-(4'-fluorophenyl)-6-(1'-methylethyl)-1H-pyrazolo[3,4-b]pyridine-5-carboxylate (Compound CXVII)

A mixture of 197 g. (1.775 moles) of Compound CXII, 497 g. (1.88 moles) of Compound CXV and 2.24 l. of absolute ethanol is refluxed for 72 hours and allowed to cool, and the ethanol is evaporated at reduced pressure to obtain a yellow-orange oil. The obtained yellow-orange oil is divided into two approximately equal halves, and each half is dissolved in the minimum amount of 7:3 methyl t-butyl ether/ethyl acetate and chromatographed on 1 kg. of 70–230 mesh ASTM silica gel. The fractions from both chromatographies containing at least substantially pure Compound CXVI or a mixture of Compounds CXVI and CXVII (as indicated by thin layer chromatography) are combined and evaporated at reduced pressure to obtain a mixture of Compounds CXVI and CXVII (549.5 g.), and the fractions from both chromatographies containing at least substantially pure Compound CXVII are combined and evaporated at reduced pressure to obtain the compound (63.5 g.).

Step 4

Ethyl 4,7-dihydro-1,3-dimethyl-4-(4'-fluorophenyl)-6-(1'-methylethyl)-1H-pyrazolo[3,4-b]pyridine-5-carboxylate (Compound CXVII)

88.4 ml. of concentrated sulfuric acid is carefully added to a solution of 549.5 g. of a mixture of Compounds CXVI and CXVII from Step 3 in 3.5 l. of absolute ethanol, and the reaction mixture is refluxed for 44 hours, allowed to cool to 20°-25° C. and poured into 9 l. of water. The mixture is carefully neutralized with sodium carbonate and extracted three times with 1.9 l. portions of diethyl ether. The diethyl ether extracts are combined, dried over anhydrous magnesium sulfate, filtered and evaporated at reduced pressure to an oil. The obtained oil is dissolved in the minimum amount of 1:1 ethyl acetate/n-hexane and chromatographed on 2 kg. of 70-230 mesh ASTM silica gel utilizing 1:1 ethyl acetate/n-hexane as the eluant. The fractions containing at least substantially pure product (as indicated by thin layer chromatography) are combined and evaporated at reduced pressure to obtain the crude product as an oil (416 g.). Unreacted starting material may be isolated from other fractions and recycled.

Step 5 (Reaction BH)

Ethyl 1,3-dimethyl-4-(4'-fluorophenyl)-6-(1'-methylethyl)-1H-pyrazolo[3,4-b]pyridine-5-carboxylate (Compound CXVIII)

239 g. (1.053 moles) of 2,3-dichloro-5,6-dicyanobenzoquinone is added over a period of 15-30 minutes to a solution of 63.5 g. of Compound CXVII from Step 3 and 308.5 g. of crude Compound CXVII from Step 4 (~1.04 moles) in 3 l. of dioxane during which the internal temperature rises from 20°-25° C. to 40° C., and the reaction mixture is stirred at 20°-25° C. for 1.5-2 hours and poured into 8 l. of saturated sodium bicarbonate solution. The basic mixture is stirred for 5 minutes at 20°-25° C. and extracted once with 1.9 l. of diethyl ether and twice with 1.4 l. portions of diethyl ether. The diethyl ether extracts are combined, dried over anhydrous magnesium sulfate, filtered and evaporated at reduced pressure to obtain a dark red oil. The obtained dark red oil is chromatographed on 1.5 kg. of 70-230 mesh ASTM silica gel utilizing methyl t-butyl ether as the eluant. The fractions containing a substantial amount of product (as indicated by thin layer chromatography) are combined and evaporated at reduced pressure to obtain a cherry red oil. The oil is dissolved in 800 ml. of mixed hexanes, and the solution is maintained at 0° C. for 16 hours and at −20° C. for 30 minutes. The precipitate is collected by filtration, washed with 400 ml. of cold (0°-5° C.) n-hexane and dried to constant weight at 10-30 mm. Hg and 20°-25° C. to obtain the product (206 g.), m.p. 68°-71° C.

Step 6 (Reaction AA)

1,3-Dimethyl-4-(4'-fluorophenyl)-6-(1'-methylethyl)-1H-pyrazolo[3,4-b]pyridine-5-methanol (Compound CXIX)

1.8 l. of 1M. diisobutylaluminum hydride/n-hexane (1.8 moles) is added dropwise over a period of 1 hour to a solution of 90 g. (0.254 mole) of Compound CXVIII in 1.45 l. of dry tetrahydrofuran stirred at 0° C. while maintaining the temperature at −5°-5° C., and the reaction mixture is allowed to warm to 20°-25° C., stirred at this temperature for 48 hours and cooled to 5° C., the reaction mixture being stirred under nitrogen throughout. 1.8 l. of saturated ammonium chloride solution is added carefully with stirring at 5° C., 950 ml. of diethyl ether is added, the mixture is filtered using some Celite ® filter aid, the organic layer is separated, and the aqueous layer is extracted twice with 950 ml. portions of diethyl ether. The diethyl ether extracts are combined with the previous organic layer, and the combined organic solution is dried over anhydrous magnesium sulfate, filtered and evaporated at reduced pressure to obtain a yellowish-white solid. The obtained solid is dissolved in 390 ml. of hot methyl t-butyl ether, filtered through a cotton plug, cooled to 0° C. and finally cooled to −20° C. The resulting solid is collected by filtration, washed with a little cold methyl t-butyl ether and vacuum dried at 50° C. to obtain the product (43 g.), m.p. 166°-168° C.

Step 7 (Reaction BA)

5-Chloromethyl-1,3-dimethyl-4-(4'-fluorophenyl)-6-(1'-methylethyl)-1H-pyrazolo[3,4-b]pyridine (Compound CXX)

A solution of 10.0 g. (31.95 mmoles) of Compound CXIX and 12.0 g. (7.5 ml., 100 mmoles) of thionyl chloride in 250 ml. of methylene chloride is refluxed for 4 hours and cooled to 20°-25° C., and the excess thionyl chloride and methylene chloride are evaporated at reduced pressure. 100 ml. of toluene is added to the residue, the toluene is evaporated at reduced pressure, and these two steps are repeated twice to obtain the crude product as an orangebrown oil.

Step 8 (Reaction BC)

Dimethyl [[1,3-dimethyl-4-(4'-fluorophenyl)-6-(1'-methylethyl)-1H-pyrazolo[3,4-b]pyrid-5-yl]methyl]phosphonate (Compound CXXI)

60 ml. of trimethyl phosphite is carefully added to the crude product of Step 7 of this example (Compound CXX) stirred at ~0° C., the reaction mixture is refluxed for 18 hours and cooled, and the excess trimethyl phosphite is evaporated at reduced pressure to obtain an orange oil which solidifies upon standing. The solid is triturated with mixed hexanes, collected by filtration and vacuum dried to obtain the product (11.24 g.). An analytical sample is obtained by recrystallization from methyl t-butyl ether. M.p. 153°-154° C.

Step 9 (Reaction G)

1,1-Dimethylethyl (3R,5S)-(E)-7-[1',3'-dimethyl-4'-(4"-fluorophenyl)-6'-(1"-methylethyl)-1H-pyrazolo[3,4-b]pyrid-5'-yl]-3,5-di-[(1',1'-dimethylethyl)diphenylsilyloxy]hept-6-enoate (Compound CXXII)

16 ml. of 1.6M. n-butyllithium/hexane (25.6 mmoles) is added rapidly dropwise to a solution of 10 g. (24.7 mmoles) of Compound CXXI in 100 ml. of dry tetrahydrofuran stirred at −78° C., the resulting orange solution is stirred at −78° C. for 10 minutes, a solution of 18 g. (24.7 mmoles) of Compound CIX in ~65 ml. of dry tetrahydrofuran is added rapidly dropwise with stirring at −78° C., the resulting pale yellow solution is stirred at −78° C. for 15 minutes, 20 ml. of 1.5M. lithium dissopropylamide bis(tetrahydrofuran) complex/cyclohexane (30 mmoles) is added via syringe with stirring at −78° C., and the reaction mixture is allowed to warm to 20°–25° C. with stirring and is stirred at 20°–25° C. for 30 minutes, the reaction mixture being stirred under argon throughout. The reaction mixture is poured into a mixture of 800 ml. of water and 150 ml. of saturated ammonium chloride solution, and the mixture is extracted three times with diethyl ether. The diethyl ether extracts are combined, dried over anhydrous magnesium sulfate, filtered and evaporated at reduced pressure to obtain an orange oil. The obtained oil is flash chromatographed on 230–400 mesh ASTM silica gel utilizing 4:1 mixed hexanes/methyl t-butyl ether as the eluant, and the fractions containing the product (as indicated by thin layer chromatography) are combined and evaporated at reduced pressure to obtain the 99% pure product as a yellow-orange resin (16.6 g.).

Step 10 (Reaction H)

1,1-Dimethylethyl (3R,5S)-(E)-3,5-dihydroxy-7-[1',3'-dimethyl-4'-(4"-fluorophenyl)-6'-(1"-methylethyl)-1H-pyrazolo[3,4-b]pyrid-5'-yl]hept-6-enoate (Compound CXXIII)

A solution of 32.7 g. (33.6 mmoles) of Compound CXXII in 200 ml. of acetonitrile is added rapidly dropwise to a mixture of 107 g. (340 mmoles) of tetra-n-butylammonium fluoride.trihydrate, 500 ml. of acetonitrile and 20.4 g. (340 mmoles) of glacial acetic acid stirred at 45°–50° C., and the reaction mixture is stirred at 60°–65° C. for 48 hours, the reaction mixture being stirred under argon throughout. The reaction mixture is poured into a mixture of 150 ml. of saturated sodium chloride solution, 200 ml. of saturated sodium carbonate solution and 1.35 l. of water (the pH of the mixture should be ~7.5–8.5 after the addition), and the mixture is extracted three times with diethyl ether. The diethyl ether extracts are combined, washed three times with 500 ml. portions of water, dried over anhydrous magnesium sulfate, filtered and evaporated at reduced pressure to an orange oil. The obtained oil is flash chromatographed on 230–400 mesh ASTM silica gel utilizing 7:3 mixed hexanes/ethyl acetate as the eluant. The fractions containing the product (as indicated by thin layer chromatography) are combined and evaporated at reduced pressure to obtain the product as a resin (8.42 g.).

N.M.R. (CDCl$_3$): 1.33–1.37 (d, 6H), 1.51 (s, 9H), 1.97 (s, 3H), 2.32–2.40 (m, 2H), 3.39–3.53 (m, 1H), 4.12 (s, 3H), 4.31–4.45 (m, 1H), 5.26–5.38 (dd, 1H), 6.50–6.59 (d, 1H), 7.08–7.31 (m, 4H).

EXAMPLE 2

Sodium (3R,5S)-(E)-3,5-dihydroxy-7-[1',3'-dimethyl-4'-(4"-fluorophenyl)-6'-(1"-methylethyl)-1H-pyrazolo[3,4-b]pyrid-5'-yl]hept-6-enoate (Reaction K)

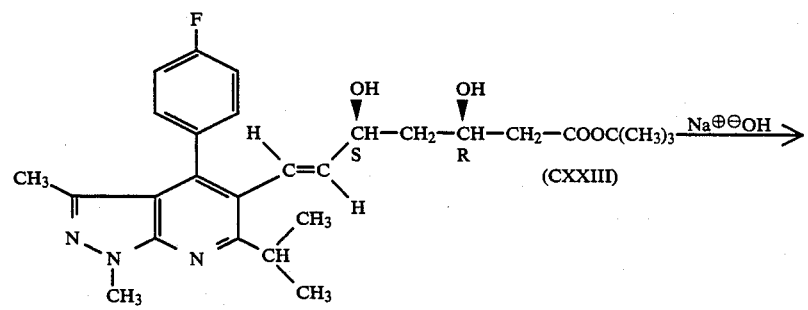

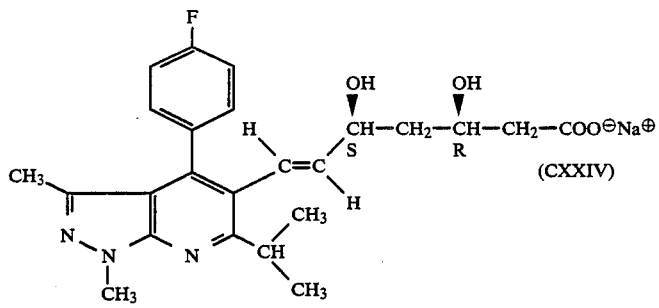

A mixture of 8.3 g. (16.7 mmoles) of Compound CXXIII, 16.5 ml. of 1N. sodium hydroxide solution (16.5 mmoles) and 150 ml. of ethanol is stirred at 20°–25° C. under nitrogen for 3.5 hours, the solvent is evaporated at reduced pressure to obtain a brown foamy resin ∼75 ml. of diethyl ether is added, the inside wall of the reaction flask is rinsed with ∼15 ml. of chloroform so as to triturate the foamy resin, and the resulting yellow light brown powder is collected by filtration and vacuum dried for 4 hours to obtain the product (7.59 g.), m.p. 199°–203° C. (dec.). A previous batch had a melting point of 169°–175° C. (dec.).

N.M.R. (CD$_3$OD): 1.16–1.40 (m, 1H), 1.3–1.34 (d, 6H), 1.42–1.61 (m, 1H), 1.90 (s, 3H), 2.10–2.32 (m, 2H), 3.48–3.53 (m, 1H), 3.63–3.78 (m, 1H), 4.02 (s, 3H), 4.19–4.29 (m, 1H), 5.33–5.44 (dd, 1H), 6.47–6.56 (d, 1H), 7.11–7.38 (m, 4H).

EXAMPLE 3

Ethyl erythro-(E)-3,5-dihydroxy-7-[1',6'-dimethyl-4'-(4''-fluorophenyl)-3'-phenyl-1H-pyrazolo[3,4-b]pyrid-5'-yl]-hept-6-enoate

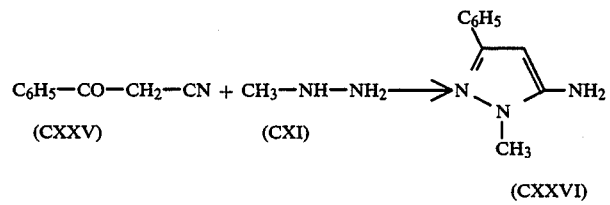

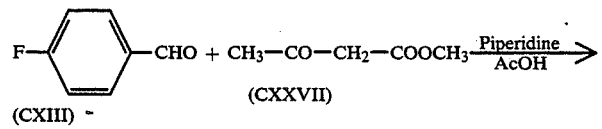

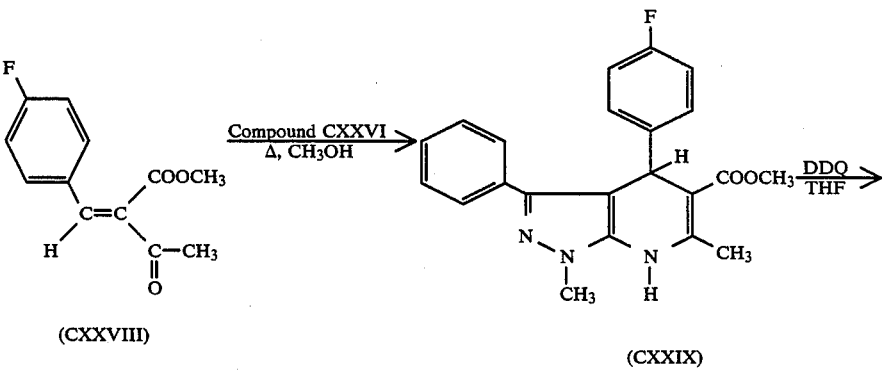

-continued

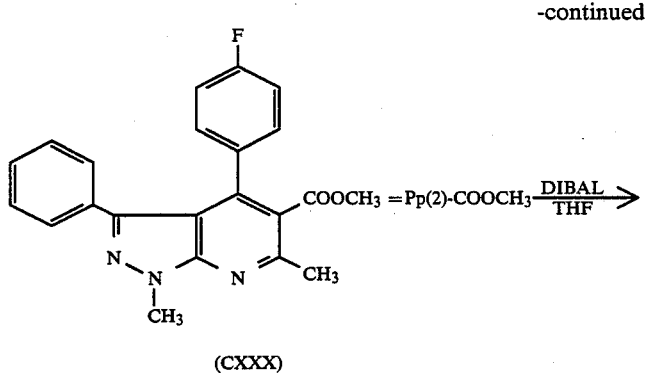
(CXXX)

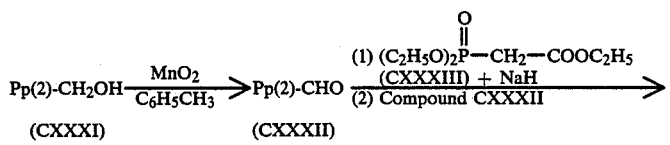

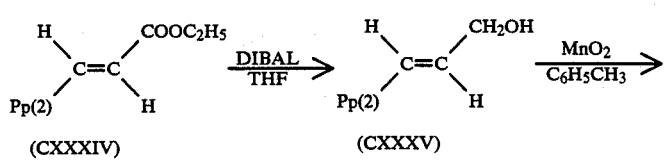

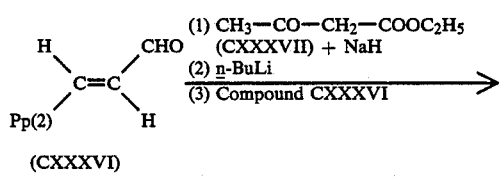

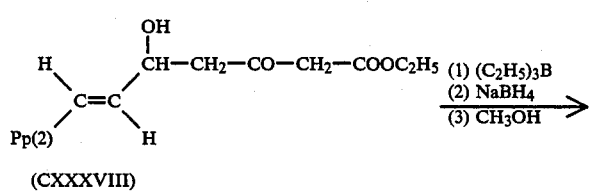

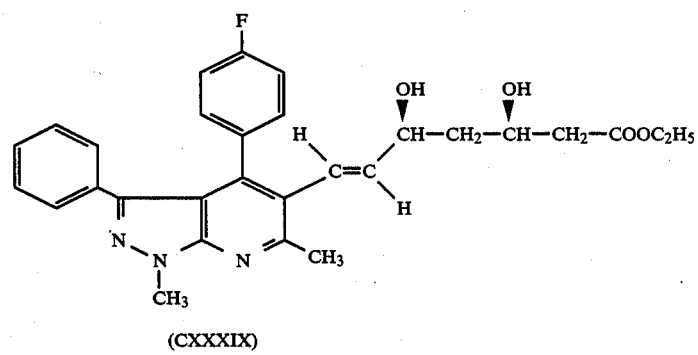
(CXXXIX)

Step 1

5-Amino-1-methyl-3-phenylpyrazole (Compound CXXVI)

A mixture of 11.0 g. (75.9 mmoles) of benzoylacetonitrile, 3.5 g. (75.9 mmoles) of methylhydrazine and 25 ml. of isopropanol is refluxed under nitrogen for 24 hours, allowed to cool to 20°–25° C. and evaporated at reduced pressure. The residual oil is triturated with toluene, and the obtained solid is collected by filtration and vacuum dried to obtain the product as a yellow powder (9.3 g. (70.9%)), m.p. 124°–128° C.

Step 2

Methyl (Z)-2-[(4'-fluorophenyl)methylene]-3-oxobutanoate (Compound CXXVIII)

A mixture of 100.0 g. (86.4 ml., 0.806 mole) of 4-fluorobenzaldehyde, 93.6 g. (87.0 ml., 0.806 mole) of methyl acetoacetate, 7 ml. of glacial acetic acid, 7.0 g. of piperidine and 900 ml. of toluene is refluxed for 16 hours utilizing a Dean-Stark apparatus to remove the water that forms, allowed to cool to 20°–25° C., washed successively four times with 125 ml. portions of 5% sdium hydroxide solution, four times with 125 ml. portions of 10% sodium bisulfite solution and four times with 250 ml. portions of water, dried over anhydrous magnesium sulfate, filtered and evaporated at reduced pressure. The residue is chromatographed on 230–400 mesh ASTM silica gel utilizing 1:1 ethyl acetate/mixed hexanes as the eluant. The fractions containing the product (as indicated by thin layer chromatography) are combined, evaporated at reduced pressure and vacuum distilled at 0.18 mm. Hg to obtain the crude product as a dense yellow oil (94.6 g.). B.p. 114°–115° C./0.18 mm. Hg. (The obtained crude product contains two components according to thin layer chromatography, the second probably being the corresponding (E) compound.)

Step 3

Methyl 4,7-dihydro-1,6-dimethyl-4-(4'-fluorophenyl)-3-phenyl-1H-pyrazolo[3,4-b]pyridine-5-carboxylate (Compound CXXIX)

A mixture of 5.3 g. (30.6 mmoles) of Compound CXXVI, 6.2 g. (27.8 mmoles) of Compound CXXVIII and 25 ml. of HPLC grade methanol is refluxed under nitrogen for 16 hours and stirred at 20°–25° C. for 64 hours. The solidified mixture is dissolved in 20 ml. of HPLC grade methanol and refluxed under nitrogen for 72 hours, allowed to cool to 20°–25° C. and evaporated at reduced pressure. The residue is triturated with diethyl ether, and the obtained solid is collected by filtration and vacuum dried to obtain the product (0.82 g.). The filtrate is evaporated at reduced pressure, and the residue is flash chromatographed on 230–400 mesh ASTM silica gel utilizing methylene chloride to elute two contaminants and ethyl acetate to elute the product. The fractions containing the product (as indicated by thin layer chromatography) are combined and evaporated at reduced pressure, and the residue is triturated with diethyl ether to obtain additional product (5.88 g.), m.p. 181°–183° C. Total yield: 6.7 g. (64%).

Step 4 (Reaction BH)

Methyl 1,6-dimethyl-4-(4'-fluorophenyl)-3-phenyl-1H-pyrazolo[3,4-b]pyridine-5-carboxylate (Compound CXXX)

A mixture of 6.6 g. (17.5 mmoles) of Compound CXXIX, 4.0 g. (17.6 mmoles) of 2,3-dichloro-5,6-dicyano-1,4-benzoquinone and 20 ml. of dry tetrahydrofuran is stirred at 20°–25° C. for 1 hour, an additional 0.4 g. (1.76 mmoles) of 2,3-dichloro-5,6-dicyano-1,4-benzoquinone is added, and the reaction mixture is stirred at 20°–25° C. for 1 hour, the reaction mixture being stirred under nitrogen throughout. The solvent is evaporated at reduced pressure, and the residue is flash chromatographed of 230–400 mesh ASTM silica gel utilizing 1:1 methyl t-butyl ether/mixed hexanes as the eluant. The fractions containing the pure product (as determined by thin layer chromatography) are combined and evaporated at reduced pressure, and the residue is triturated with mixed hexanes. The obtained solid is collected by filtration and vacuum dried to obtain the product (4.0 g.), m.p. 142°–144° C. An additional 0.6 g. of less pure product is similarly obtained from other chromatography fractions.

Step 5 (Reaction AA)

1,6-Dimethyl-4-(4'-fluorophenyl)-3-phenyl-1H-pyrazolo[3,4-b]pyridine-5-methanol (Compound CXXXI)

48.0 ml. of 1M. diisobutylaluminum hydride (48 mmoles) is added rapidly dropwise to a solution of 4.5 g. (12.0 mmoles) of Compound CXXX in 35 ml. of dry tetrahydrofuran stirred at 0° C., and the reaction mixture is allowed to warm to 20°–25° C., stirred at 20°–25° C. for 4 hours and cooled to 0° C., the reaction mixture being stirred under nitrogen throughout. The reaction mixture is quenched with saturated ammonium chloride solution, acidified to pH ~6 with 2N. hydrochloric acid and extracted three times with methyl t-butyl ether. The methyl t-butyl ether extracts are combined, dried over anhydrous magnesium sulfate, filtered and evaporated at reduced pressure. The residue is triturated with mixed hexanes to obtain the yellow crystalline crude product (1.1 g.). The aqueous layer from the methyl t-butyl ether extractions is extracted with methylene chloride, the methylene chloride extract is evaporated at reduced pressure, and the residue is triturated with mixed hexanes to obtain additional product as white crystals (1.1 g.), m.p. 231°–236° C. An additional 0.1 g. of impure product may be obtained from the various mother liquors.

Step 6 (Reaction AB)

1,6-Dimethyl-4-(4'-fluorophenyl)-3-phenyl-1H-pyrazolo[3,4-b]pyridine-5-carboxaldehyde (Compound CXXXII)

A mixture of 2.4 g. (6.9 mmoles) of Compound CXXXI, 10.0 g. (115 mmoles) of activated manganese dioxide and 25 ml. of toluene is refluxed for 16 hours, allowed to cool to 20°–25° C. and filtered through Celite ® filter aid. The Celite ® is rinsed with diethyl ether, the diethyl ether rinse is combined with the toluene filtrate, the solvent is evaporated at reduced pressure, the residue is triturated with mixed hexanes, and the solid is collected by filtration and vacuum dried to obtain the product (1.44 g.). An additional 0.26 g. of product may be obtained from the mother liquor.

Step 7 (Reaction AF)

Ethyl (E)-3-[1',6'-dimethyl-4'-(4''-fluorophenyl)-3'-phenyl-1H-pyrazolo[3,4-b]pyrid-5'-yl]propenoate (Compound CXXXIV)

0.3 g. of 60% sodium hydride/mineral oil (7.5 mmoles) is washed with mixed hexanes and suspended in 3 ml. of dry tetrahydrofuran, the suspension is cooled to 0° C., a solution of 1.5 ml. (1.7 g., 7.6 mmoles) of triethylphosphonoacetate in 5 ml. of dry tetrahydrofuran is added rapidly dropwise, the mixture is stirred at 0° C. for 1 hour, a solution of 1.7 g. (4.9 mmoles) of Compound CXXXII in 17 ml. of dry tetrahydrofuran is added rapidly dropwise, and the reaction mixture is allowed to warm to 20°–25° C. and stirred at this temperature for 16 hours, the reaction mixture being stirred under nitrogen throughout. The reaction mixture is poured into water, and the mixture is extracted three times with diethyl ether. The diethyl ether extracts are combined, dried over anhydrous magnesium sulfate, filtered and evaporated at reduced pressure. The residue is triturated with cold mixed hexanes, and the resulting solid is collected by filtration and vacuum dried to obtain the crude product (1.54 g.).

Step 8 (Reaction AG)

(E)-3-[1',6'-Dimethyl-4'-(4''-fluorophenyl)-3'-phenyl-1H-pyrazolo[3,4-b]pyrid-5'-yl]prop-2-en-1-ol (Compound CXXXV)

14.4 ml. of 1M. diisobutylaluminum hydride/tetrahydrofuran (14.4 mmoles) is added rapidly dropwise to a solution of 1.5 g. (3.6 mmoles) of Compound CXXXIV in 10 ml. of dry tetrahydrofuran stirred at 0°–5° C., and the reaction mixture is allowed to warm to 20°–25° C. and stirred at 20°–25° C. for 16 hours, the reaction mixture being stirred under nitrogen throughout. The reaction mixture is quenched with saturated ammonium chloride solution, acidified to pH ~6 with 2N. hydrochloric acid and extracted three times with diethyl ether. The diethyl ether extracts are combined, dried over anhydrous magnesium sulfate, filtered and evaporated at reduced pressure to obtain the crude product as a white powder (1.2 g.).

Step 9 (Reaction AH)

(E)-3-[1',6'-Dimethyl-4'-(4''-fluorophenyl)-3'-phenyl-1H-pyrazolo[3,4-b]pyrid-5'-yl]prop-2-en-1-al (Compound CXXXVI)

A mixture of 1.2 g. (3.2 mmoles) of Compound CXXXV, 4.8 g. (55.2 mmoles) of activated manganese dioxide and 40 ml. of toluene is refluxed for 16 hours and, while hot, filtered through Celite ® filter aid. The Celite ® is washed with 1:1 diethyl ether/methylene chloride, and the washing is combined with the previous filtrate. The combined organic solution is evaporated at reduced pressure, and the residue is triturated with cold mixed hexanes. The resulting solid is collected by filtration and vacuum dried to obtain the crude product (0.5 g.). Additional crude product (0.6 g.) may be obtained from the mother liquor.

Step 10 (Reaction A)

Ethyl (±)-(E)-7-[1',6'-dimethyl-4'-(4''-fluorophenyl)-3'-phenyl-1H-pyrazolo[3,4-b]pyrid-5'-yl]-5-hydroxy-3-oxohept-6-enoate (Compound CXXXVIII)

(a) 0.6 g. of sodium hydride/mineral oil (15 mmoles) is rinsed with hexane and suspended in 10 ml. of dry tetrahydrofuran, a solution of 1.9 ml. (1.94 g., 14.9 mmoles) of ethyl acetoacetate in 5 ml. of dry tetrahydrofuran is added dropwise with stirring at 0° C., the reaction mixture is stirred at 0° C. for 20 minutes, 9.6 ml. of 1.55M. n-butyllithium/hexane (14.9 mmoles) is added dropwise with stirring at 0° C., and the reaction mixture is stirred at 0° C. for 20 minutes and cooled to −20° C., the reaction mixture being stirred under nitrogen throughout.

(b) ~60% of the dianion solution of Part (a) of this step (~9 mmoles) is added via syringe to a solution of 1.1 g. (~2.96 mmoles) of crude Compound CXXXVI in 15 ml. of dry tetrahydrofuran stirred at −20° C., and the reaction mixture is stirred at −20° C. for 20 minutes, the reaction mixture being stirred under nitrogen throughout. The reaction mixture is poured into a mixture of 50 ml. of saturated ammonium chloride solution and 50 ml. of water, and the mixture is extracted three times with diethyl ether. The diethyl ether extracts are combined, dried over anhydrous magnesium sulfate, filtered and evaporated at reduced pressure. The residue is flash chromatographed on 230–400 mesh ASTM silica gel utilizing 1:1 methyl t-butyl ether/mixed hexanes as the eluant, and the fractions containing the product (as indicated by thin layer chromatography) are combined and evaporated at reduced pressure to obtain the product as a yellow solid (0.7 g.).

Step 11 (Reaction B)

Ethyl (±)-erythro-(E)-3,5-dihydroxy-7-[1',6'-dimethyl-4'-(4''-fluorophenyl)-3'-phenyl-1H-pyrazolo[3,4-b]pyrid-5'-yl]-hept-6-enoate (Compound CXXXIX)

(a) 1.7 ml. of 1.0M. triethylborane/tetrahydrofuran (1.7 mmoles) is added rapidly dropwise to a solution of 0.7 g. (1.4 mmoles) of Compound CXXXVIII in 5 ml. of 4:1 tetrahydrofuran/methanol stirred at 20°–25° C., the reaction mixture is stirred at 20°–25° C. for 1 hour and cooled to −70° C., 0.06 g. (1.6 mmoles) of sodium borohydride is added in one portion, and the reaction mixture is stirred at −70° C. for 3 hours, the reaction mixture being stirred under nitrogen throughout. The reaction mixture is quenched with 4 ml. of saturated ammonium chloride solution and allowed to warm to 20°–25° C., sufficient water to dissolve all solids is added, and the mixture is extracted twice with diethyl ether. The diethyl ether extracts are combined, dried over anhydrous magnesium sulfate, filtered and evaporated at reduced pressure to obtain the cyclic boron ester.

(b) A solution of the product of Part (a) of this step in 5 ml. of methanol is stirred at 20°–25° C. for 16 hours and evaporated at reduced pressure, and the residue is dissolved in diethyl ether. The diethyl ether solution is washed twice with saturated sodium chloride souution, dried over anhydrous magnesium sulfate, filtered and evaporated at reduced pressure, and the residual oil is chromatographed on 230–400 mesh ASTM silica gel utilizing 3:2:1 ethyl acetate/methyl t-butyl ether/mixed hexanes and then ethyl acetate as the eluant. The fractions containing the product (as indicated by thin layer chromatography) are combined and evaporated at reduced pressure to obtain the product (0.29 g.).

N.M.R. (CDCl$_3$): 1.26–1.32 (t, 3H), 2.39–2.47 (m, 2H), 2.72 (s, 3H), 4.20 (s, 3H), 4.28–4.43 (m, 1H), 5.27–5.38 (dd, 1H), 6.46–6.54 (d, 1H), 6.68–6.83 (t, 2H), 6.86–7.20 (m, 7H).

The product is at least 95% pure erythro racemate; any threo racemate present therein may be separated therefrom by conventional means. The erythro racemate may be resolved into two optically pure enantiomers, the 3R,5S and 3S,5R enantiomers, of which the former is preferred. Any threo racemate may be resolved to obtain the 3R,5R and 3S,5S enantiomers. The use of a non-stereoselective reduction would afford a mixture of all four stereoisomers wherein the ratio of the erythro stereoisomers to the threo stereoisomers ranges from 3:2 to 2:3.

EXAMPLE 4

Sodium (+)-erythro-(E)-3,5-dihydroxy-7-[1',6'-dimethyl-4'-(4''-fluorophenyl)-3'-phenyl-1H-pyrazolo[3,4-b]pyrid-5'-yl]-hept-6-enoate (Reaction K)

solution is gently washed with diethyl ether, the residual ether in the aqueous solution is evaporated at reduced pressure, and the aqueous solution is lyophilized to obtain the product (0.2 g.), m.p. 210°–225° C. (dec.).

N.M.R. (CD$_3$OD): 1.25–1.41 (m, 1H), 1.49–1.66 (m, 1H), 2.12–2.33 (m, 2H), 2.74 (s, 3H), 3.71–3.88 (m, 1H), 4.17 (s, 3H), 5.34–5.48 (dd, 1H), 6.42–6.52 (d, 1H), 6.72–7.23 (m, 9H).

The product is at least 95% pure erythro racemate; any threo racemate present therein may be separated therefrom by conventional means. The erythro racemate may be resolved into two optically pure enantiomers, the 3R,5S and 3S,5R enantiomers, of which the former is preferred. Any threo racemate may be resolved to obtain the 3R,5R and 3S,5S enantiomers. The

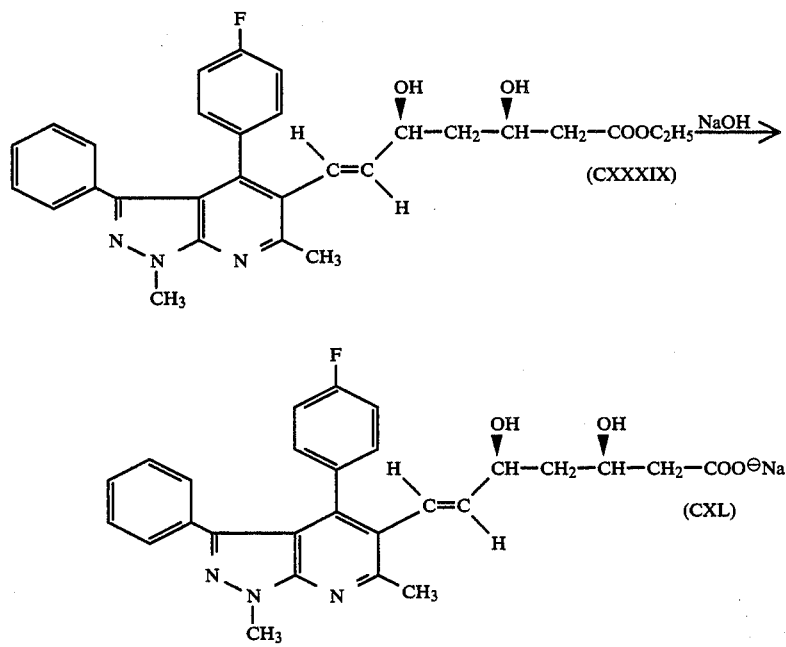

A mixture of 0.21 g. (0.42 mmole) of Compound CXXXIX, 0.8 ml. of 0.5N. sodium hydroxide solution (0.4 mmole) and 5 ml. of absolute ethanol is stirred at 20°–25° C. under nitrogen for 1.5 hours, the solvent is evaporated at reduced pressure, and the residue is dissolved in 2 ml. of water (the minimum amount). The use of a starting material synthesized by using a non-stereoselective reduction in Step 11 of Example 3 would afford a mixture of all four stereoisomers wherein the ratio of the erythro stereoisomers to the threo stereoisomers ranges from 3:2 to 2:3.

TABLE I

Examples 5–9
The following additional compounds of Groups IAa and ICa may be synthesized by the processes set forth above:

|  | R$_1$ | R$_2$ | R$_3$ | R$_4$ | X | R$_{17}$ | R$_{18}$ | Isomers | M.p. |
|---|---|---|---|---|---|---|---|---|---|
| Ex. 5 | CH$_3$ | 4-fluorophenyl | CH$_3$ | CH$_3$ | (E)—CH=CH— | H | C$_2$H$_5$ | E | Solid foam |
| Ex. 6 | CH$_3$ | 4-fluorophenyl | CH$_3$ | CH$_3$ | (E)—CH=CH— | H | Na$^\oplus$ | E | Solid foam |
| Ex. 7 | i-C$_3$H$_7$ | 4-fluorophenyl | CH$_3$ | CH$_3$ | (E)—CH=CH— | H | C$_2$H$_5$ | E | Oil |
| Ex. 8 | i-C$_3$H$_7$ | 4-fluorophenyl | CH$_3$ | CH$_3$ | (E)—CH=CH— | H | Na$^\oplus$ | E | Solid foam |
| Ex. 9 | i-C$_3$H$_7$ | cyclohexyl | CH$_3$ | CH$_3$ | (E)—CH=CH— | H | C$_2$H$_5$ | E | Oil |

E = erythro racemate ($\geqq$95% pure; balance, if any, threo racemate and/or impurities)

TABLE II

Example 10
The following compound of Group IAb may be synthesized by the processes set forth above:

| | $R_1$ | $R_2$ | $R_3$ | $R_4$ | X | $R_{17}$ | Isomers | M.p. |
|---|---|---|---|---|---|---|---|---|
| Ex. 10 | $CH_3$ | 4-fluorophenyl | $CH_3$ | $CH_3$ | (E)—CH=CH— | H | trans | Solid foam | trans = trans lactone racemate (≧95% pure; balance, if any, cis lactone racemate and/or impurities)

| N.M.R. Data | |
|---|---|
| Ex. 5 (CDCl$_3$): | 1.26–1.34 (t, 3H), 1.93 (s, 3H), 2.41–2.46 (m, 2H), 2.68 (s, 3H), 4.07 (s, 3H), 4.13–4.23 (q, 2H), 4.28–4.41 (m, 1H), 5.30–5.40 (dd, 1H), 6.36–6.46 (d, 1H), 7.04–7.27 (m, 4H) |
| Ex. 6 (CD$_3$OD): | 1.28–1.37 (m, 1H), 1.46–1.64 (m, 1H), 1.88 (s, 3H), 2.11–2.32 (m, 2H), 2.69 (s, 3H), 4.01 (s, 3H), 4.15–4.30 (m, 1H), 5.37–5.48 (dd, 1H), 6.36–6.47 (d, 1H), 7.12–7.37 (m, 4H) |
| Ex. 7 (CDCl$_3$): | 1.92 (s, 3H), 2.38–2.46 (m, 2H), 3.32–3.49 (m, 1H), 4.06 (s, 3H), 4.13–4.25 (q, 2H), 4.23–4.41 (m, 1H), 5.22–5.33 (dd, 1H), 6.46–6.53 (d, 1H), 7.00–7.30 (m, 4H) |
| Ex. 8 (CDCl$_3$ + CD$_3$OD): | 1.29–1.33 (d, 6H), 1.91 (s, 3H), 2.12–2.37 (m, 2H), 3.37–3.54 (m, 1H), 3.81–3.96 (m, 1H), 4.04 (s, 3H), 5.26–5.37 (dd, 1H), 6.42–6.51 (d, 1H), 7.04–7.28 (m, 4H) |
| Ex. 9 (CDCl$_3$): | 1.15–1.4 (m, 9H), 1.58–2.10 (m, 10H), 2.73 (s, 3H), 3.22–3.45 (m, 1H), 4.01 (s, 3H), 4.10–4.27 (q, 2H), 4.32–4.47 (m, 1H), 5.64–5.78 (m, 1H), 6.80–6.89 (d, 1H) |
| Ex. 10 (CDCl$_3$): | 1.93 (s, 3H), 2.50–2.78 (m, 2H), 2.68 (s, 3H), 4.07 (s, 3H), 4.18–4.29 (m, 1H), 5.04–5.17 (m, 1H), 5.32–5.43 (dd, 1H), 6.46–6.54 (d, 1H), 7.06–7.28 (m, 4H) |

Any threo racemate present in Examples 5–9 may be isolated therefrom and resolved to obtain the 3R,5R and 3S,5S enantiomers, and each erythro racemate may be resolved to obtain the 3R,5S and 3S,5R enantiomers, of which in each case the former is preferred.

Any cis racemate present in Example 10 may be isolated therefrom and resolved to obtain the 4R,6R and 4S,6S enantiomers, and the trans racemate may be resolved to obtain the 4R,6S and 4S,6R enantiomers, the former being preferred in each case.

Each of the compounds of the examples wherein Z is a group of Formula a wherein $R_{18}$ is a cation may be converted into the corresponding compounds wherein $R_{18}$ is hydrogen or a different cation M, particularly the latter, expecially M', by the processes set forth in Reaction Scheme III.

Each of Examples 1–10 (including each of the possible optical isomers of each example) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

Throughout the specification, the term "reduced pressure" denotes aspirator pressure. Where no solvent is specified in connection with a solution, the solvent is water, and all solvent mixtures are by volume. When a reaction is carried out under nitrogen or argon, dry nitrogen or argon, as the case may be, is used to maintain anhydrous conditions (except where the reaction medium contains water).

All nuclear magnetic resonance spectra were taken at ambient temperature on a 200 MHz. spectrometer. All chemical shifts are given in p.p.m. (δ) relative to tetramethylsilane, and where a single δ value is given for anything other than a sharp singlet, it is its center point. In the N.M.R. data:
 d = doublet
 dd = doublet of a doublet
 m = multiplet
 q = quartet
 s = singlet
 t = triplet

What is claimed is:

1. A compound of the formula wherein
$R_1$ is $C_{1-6}$alkyl not containing an asymmetric carbon atom, $C_{5-7}$cycloalkyl, ($C_{5-7}$cycloalkyl)methyl, phenyl-$(CH_2)_m$-, pyridyl-2, pyridyl-3, pyridyl-4, thienyl-2, thienyl-3 or $R_2$ is $C_{1-6}$alkyl not containing an asymmetric carbon atom, $C_{5-7}$cycloalkyl, ($C_{5-7}$cycloalkyl)methyl, phenyl-$(CH_2)_m$-, pyridyl-2, pyridyl-3, pyridyl-4, thienyl-2, thienyl-3 or with the proviso that not more than one of $R_1$ and $R_2$ is a member of the group consisting of pyridyl-2, pyridyl-3, pyridyl-4, thienyl-2, thienyl-3, Ring A and Ring B, $R_3$ is $C_{1-6}$alkyl not containing an asymmetric carbon atom, $C_{5-7}$cycloalkyl or

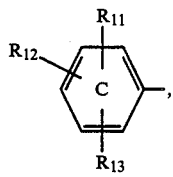

$R_4$ is $C_{1-6}$alkyl not containing an asymmetric carbon atom, $C_{5-7}$cycloalkyl or

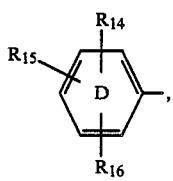

X is $-(CH_2)_n-$, $-CH=CH-$, $-CH_2-CH=CH-$ or $-CH=CH-CH_2-$, wherein n is 1, 2 or 3, and
Z is

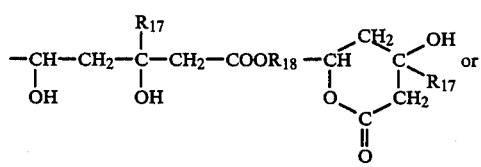

wherein
$R_{17}$ is hydrogen or $C_{1-3}$alkyl, and
$R_{18}$ is hydrogen, $R_{19}$ or M,
wherein
$R_{19}$ is a physiologically acceptable ester group, and
M is a cation,
with the proviso that Z may be a group of the formula

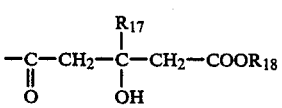

only when (i) X is $-CH=CH-$ or $-CH_2-CH=CH-$, (ii) $R_{17}$ is $C_{1-3}$alkyl or (iii) both (i) and (ii), wherein
each of $R_5$, $R_8$, $R_{11}$ and $R_{14}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy,
each of $R_6$, $R_9$, $R_{12}$ and $R_{15}$ is independently hydrogen, $C_{1-3}$alkyl, $C_{1-3}$alkoxy, trifluoromethyl, fluoro, chloro, phenoxy or benzyloxy, and
each of $R_7$, $R_{10}$, $R_{13}$ and $R_{16}$ is independently hydrogen, $C_{1-2}$alkyl, $C_{1-2}$alkoxy, fluoro or chloro, with the provisos that not more than one substituent on each of Rings A, B, C and D independently is trifluoromethyl, not more than one substituent on each of Rings A, B, C and D independently is phenoxy, and not more than one substituent on each of Rings A, B, C and D independently is benzyloxy, and
each m is independently 1, 2 or 3.

2. A compound according to claim 1 wherein M is a pharmaceutically acceptable cation.

3. A compound according to claim 2 wherein
$R_1$ is $C_{1-6}$alkyl not containing an asymmetric carbon atom, $C_{5-7}$cycloalkyl, ($C_{5-7}$cycloalkyl)methyl or phenyl-$(CH_2)_m$-,
$R_2$ is pyridyl-2, pyridyl-3, pyridyl-4, thienyl-2, thienyl-3 or

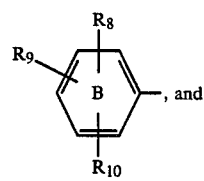, and

Z is

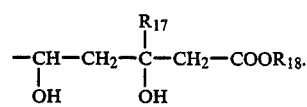

4. A compound according to claim 3 wherein
$R_1$ is $C_{1-6}$alkyl not containing an asymmetric carbon atom,
$R_2$ is

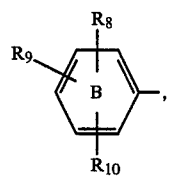, $R_3$ is $C_{1-4}$alkyl not containing an asymmetric carbon atom or

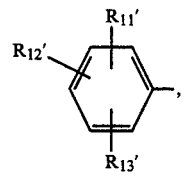

wherein
$R'_{11}$ is hydrogen, $C_{1-3}$alkyl, $C_{1-2}$alkoxy, trifluoromethyl, fluoro or chloro,
$R'_{12}$ is hydrogen, $C_{1-2}$alkyl, fluoro or chloro, and
$R'_{13}$ is hydrogen or methyl,
$R_4$ is $C_{1-4}$alkyl not containing an asymmetric carbon atom,
$R_{17}$ is hydrogen or methyl,
$R_{18}$ is hydrogen, $C_{1-3}$alkyl, n-butyl, i-butyl, t-butyl, benzyl or M, and
X is $-CH_2CH_2-$ or $-CH=CH-$.

5. A compound according to claim 4 wherein
$R_1$ is $C_{1-4}$alkyl not containing an asymmetric carbon atom,
$R_3$ is $C_{1-3}$alkyl or

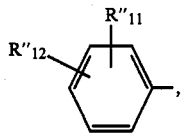

wherein
R″$_{11}$ is hydrogen, methyl or fluoro, and
R″$_{12}$ is hydrogen or methyl,
R$_4$ is C$_{1-3}$alkyl,
R$_8$ is hydrogen, C$_{1-3}$alkyl, C$_{1-2}$alkoxy, trifluoromethyl, fluoro or chloro,
R$_9$ is hydrogen, C$_{1-2}$alkyl, fluoro or chloro,
R$_{10}$ is hydrogen or methyl,
R$_{17}$ is hydrogen,
R$_{18}$ is hydrogen, C$_{1-3}$alkyl or M, and
X is (E)—CH=CH—.

6. A compound according to claim 5 wherein
R$_1$ is C$_{1-3}$alkyl,
R$_3$ is C$_{1-2}$alkyl,
R$_4$ is C$_{1-2}$alkyl,
R$_8$ is hydrogen, methyl or fluoro,
R$_9$ is hydrogen or methyl,
R$_{10}$ is hydrogen, and
R$_{18}$ is M.

7. A compound according to claim 6 wherein the hydroxy groups in the 3- and 5-positions of the group of the formula

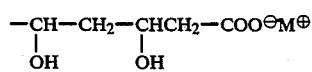

have the erythro configuration.

8. The 3R,5S enantiomer of a compound according to claim 7.

9. A compound according to claim 7 having the formula

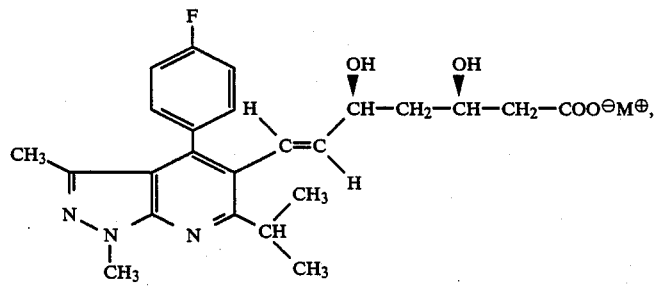

wherein M⊕ is a pharmaceutically acceptable cation.

10. The 3R,5S enantiomer of a compound according to claim 9.

11. The compound according to claim 10 having the formula

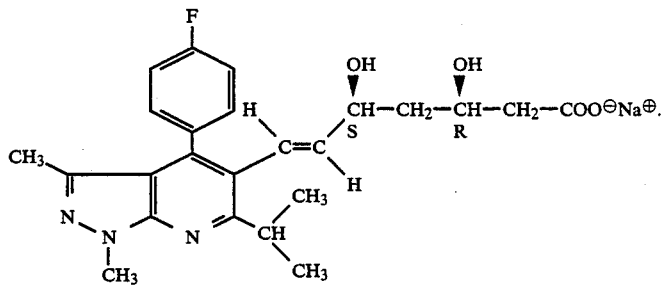

12. A compound according to claim 2 wherein
R$_1$ is C$_{1-6}$alkyl not containing an asymmetric carbon atom, C$_{5-7}$cycloalkyl, (C$_{5-7}$cycloalkyl)methyl or phenyl-(CH$_2$)$_m$-,
R$_2$ is pyridyl-2, pyridyl-3, pyridyl-4, thienyl-2, thienyl-3 or

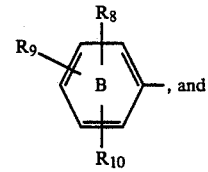

Z is

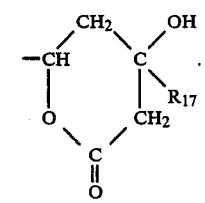

13. A compound according to claim 2 wherein
R$_1$ is C$_{1-6}$alkyl not containing an asymmetric carbon atom, C$_{5-7}$cycloalkyl, (C$_{5-7}$cycloalkyl)methyl or phenyl-(CH$_2$)$_m$-,
R$_2$ is pyridyl-2, pyridyl-3, pyridyl-4, thienyl-2, thienyl-3 or

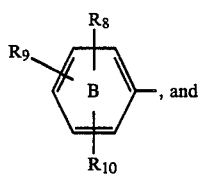

Z is

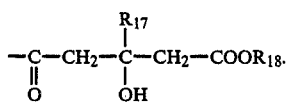

14. A compound according to claim 2 wherein R₁ is pyridyl-2, pyridyl-3, pyridyl-4, thienyl-2, thienyl-3 or

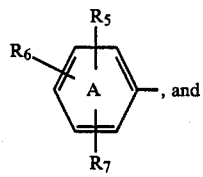

R₂ is $C_{1-6}$alkyl not containing an asymmetric carbon atom, $C_{5-7}$cycloalkyl, ($C_{5-7}$cycloalkyl) methyl or pheny-$(CH_2)_m$-.

15. A compound according to claim 2 wherein

R₁ is $C_{1-6}$alkyl not containing an asymmetric carbon atom, $C_{5-7}$cyloalkyl, ($C_{5-7}$cycloalkyl) methyl or phenyl-$(CH_2)_m$-, and R₂ is $C_{1-6}$alkyl not containing an asymmetric carbon atom, $C_{5-7}$cycloakyl, ($C_{5-7}$cycloalkyl) methyl or phenyl-$(CH_2)_m$-.

16. The compound according to claim 5 having the formula

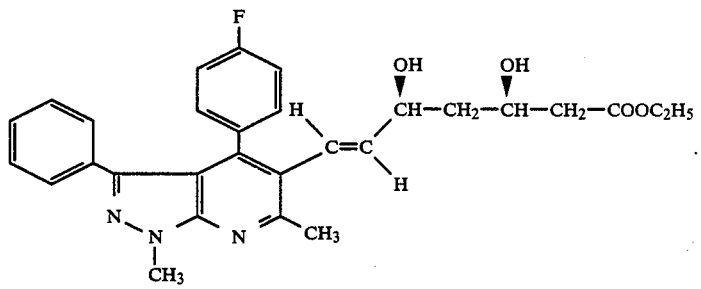

17. A composition for inhibiting cholesterol biosynthesis in a mammal comprising an effective amount of a compound according to claim 2 and a pharmaceutically acceptable carrier, said effective amount being an amount effective for inhibiting cholesterol biosynthesis in a mammal.

18. A method of inhibiting cholesterol biosynthesis comprising administering to a mammal in need of such treatment an effective amount of a compound according to claim 2, said effective amount being amount effective for inhibitng cholesterol biosynthesis.

19. A method of treating atherosclerosis comprising administering to a mammal in need of such treatment an effective amount of a compound according to claim 2, said effective amount being an amount effective for the treatment of atherosclerosis.

20. A method of treating atherosclerosis according to claim 19 comprising administering to a mammal in need of such treatment an effective amount of a compound of the formula

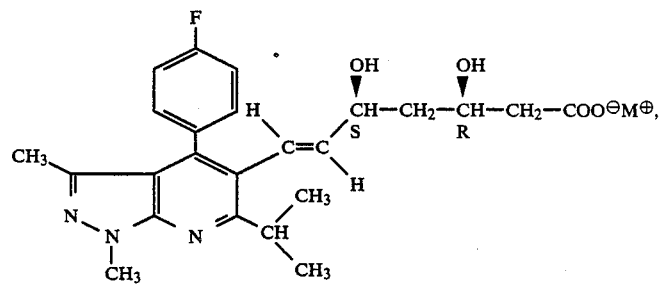

wherein M⊕ is a pharmaceutically acceptable cation, said effective amount being an amount effective for the treatment of atherosclerosis.

* * * * *